(12) United States Patent
Batt et al.

(10) Patent No.: US 9,073,928 B2
(45) Date of Patent: Jul. 7, 2015

(54) TOSYLATE SALT OF CYCLOPROPANECARBOXYLIC ACID 4-(6-CHLORO-3-METHYL-4, 10-DIHYDRO-3H-2,3,4,9-TETRABENZO[F]AZULENE-9-CARBONYL)-2-FLUOROBENZYLAMIDE

(75) Inventors: Andrzej Roman Batt, Southampton (GB); Rachel Louisa Charlotte Handy, Southampton (GB); Michael Bryan Roe, Southampton (GB); Valerie Elizabeth Peal, Cardiff (GB); Timothy John Kenhardt Gibs, Cardiff (GB); David Raymond Churchley, Weybridge (GB)

(73) Assignee: Vantia Limited, Southampton (GB)

( * ) Notice: Subject to any disclaimer, the term of this patent is extended or adjusted under 35 U.S.C. 154(b) by 235 days.

(21) Appl. No.: 13/634,704

(22) PCT Filed: Mar. 18, 2011

(86) PCT No.: PCT/GB2011/000381
§ 371 (c)(1),
(2), (4) Date: Jan. 24, 2013

(87) PCT Pub. No.: WO2011/114109
PCT Pub. Date: Sep. 22, 2011

(65) Prior Publication Data
US 2013/0281439 A1    Oct. 24, 2013

Related U.S. Application Data

(60) Provisional application No. 61/315,468, filed on Mar. 19, 2010.

(30) Foreign Application Priority Data

Mar. 19, 2010    (GB) .................................. 1004677.9

(51) Int. Cl.
A61K 31/5517    (2006.01)
C07D 487/04    (2006.01)
C07C 309/30    (2006.01)

(52) U.S. Cl.
CPC ............ *C07D 487/04* (2013.01); *C07C 309/30* (2013.01)

(58) Field of Classification Search
CPC . A61K 31/551; A61K 31/5517; C07D 487/04
USPC .......................................... 514/220; 540/557
See application file for complete search history.

(56) References Cited

FOREIGN PATENT DOCUMENTS

| EP | 1449844 | 8/2004 |
|---|---|---|
| WO | WO 03/016316 | 2/2003 |
| WO | WO 2006/021213 | 3/2006 |
| WO | WO 2007/071951 | 6/2007 |

OTHER PUBLICATIONS

Stahl et al., Handbook of Pharmaceutical Salts: Properties, Selection and Use, 2002.*
Bastin et al., "Salt Selection and Optimisation Procedures for Pharmaceutical New Chemical Entities", Organic Process Research & Development, Feb. 2000, 4, 427-435.
Bossmar et al., "Effects of SR 49059, an Orally Active V1a Vasopressin Receptor Antagonist, on Vasopressin-Induced Uterine Contractions", British Journal of Obstetrics and Gynaecology, Apr. 2007, 104(4), 471-477.
Engel et al., "Salt Form Selection and Characterization of LY333531 Mesylate Monohydrate", International Journal of Pharmaceutics, Jan. 2000, 198, 239-247.
Berge et al., "Pharmaceutical Salts", Journal of Pharmaceutical Sciences, Jan. 1977, vol. 66, No. 1, 1-19.

* cited by examiner

*Primary Examiner* — Brenda Coleman
(74) *Attorney, Agent, or Firm* — Baker & Hostetler LLP (57) ABSTRACT

The invention provides cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluene-sulphonate, pharmaceutical compositions containing it, and its use in therapy.

22 Claims, 6 Drawing Sheets

TOSYLATE SALT OF CYCLOPROPANECARBOXYLIC ACID 4-(6-CHLORO-3-METHYL-4, 10-DIHYDRO-3H-2,3,4,9-TETRABENZO[F]AZULENE-9-CARBONYL)-2-FLUOROBENZYLAMIDE

CROSS-REFERENCE TO RELATED APPLICATIONS

This application is the National Stage of International Application No. PCT/GB2011/000381, filed Mar. 18, 2011, which claims the benefit of Great Britain Application No. 1004677.9, filed Mar. 19, 2010, and U.S. Provisional Application No. 61/315,468, filed Mar. 19, 2010, the disclosures of which are incorporated herein by reference in their entireties.

The present invention relates to a salt of a vasopressin $V_{1a}$ antagonist, a pharmaceutical composition containing it and its use in therapy.

The neurophyseal hormones vasopressin (VP) and oxytocin (OT) are cyclic nonapeptides secreted by the posterior pituitary gland.

Three subtypes of the VP receptor are known and these are designated the $V_{1a}$, $V_{1b}$, and $V_2$ receptors. Only one OT receptor has so far been well characterised.

Vasopressin acts on the blood vessels, where it is a potent vasoconstrictor, and on the kidneys, where it promotes water reuptake leading to an antidiuretic effect.

The $V_{1a}$, $V_{1b}$ and $V_2$, as well as the OT receptors, are members of the super-family of seven transmembrane receptors known as G-protein coupled receptors. The $V_{1a}$ receptor mediates phospholipase C activation and intracellular calcium mobilisation. Localisation of the receptors includes blood platelets, blood vessels, hepatocytes, brain and uterus-cervix. Thus a $V_{1a}$ antagonist may have effects on any or all of these tissues. For example, selective $V_{1a}$ antagonists have been cited as having clinical utility in dysmenorrhoea, pre-term labour, hypertension, Raynaud's disease, brain oedema, motion sickness, hyperlipemia, small cell lung cancer, depression, anxiety, hyponatremia, liver cirrhosis and congestive heart failure.

With respect to dysmenorrhoea it has been proposed that myometrial activity is markedly increased in women with dysmenorrhoea during menstruation. It is proposed that the myometrial ischemia caused by increased uterine contractility might explain the menstrual pain. Furthermore, on the first day of menstruation, higher plasma concentrations of vasopressin have been measured in dysmenorroeic women than in controls.

In healthy women without dysmenorrhoea, intravenous infusion of lysine-vasopressin resulted in decreased uterine blood flow, increased uterine contractility and slight to moderate dysmenorrhoea-like pain, these effects being inhibited by a selective human $V_{1a}$ receptor antagonist (Bossmar, T. et al., *British Journal of Obstetrics and Gynaecology* (1997 April), 104(4), 471-7). Also, it is known that vasopressin contracts human uterine arteries in a dose-dependent and $V_{1a}$-mediated fashion.

The above evidence suggests that a $V_{1a}$ antagonist would be an appropriate and effective treatment for dysmenorrhoea (primary dysmenorrhoea and/or secondary dysmenorrhoea). Further evidence is taken from the clinical study carried out on the selective $V_{1a}$ antagonist SR49059 ("Effect of SR49059, an orally active $V_{1a}$ vasopressin receptor antagonist, in the prevention of dysmenorrhea". Brouard, R. et al., *British Journal of Obstetrics and Gynaecology* (2000), 107 (5), 614-619). It was found that there was a dose-related decrease in pain and a dose-related decrease in the amount of additional pain-killer taken compared to patients taking placebo.

International Patent Application WO 03/016316 A1, published 27 Feb. 2003, discloses a number of compounds which are claimed to be oxytocin agonists and to find use in the treatment of male erectile dysfunction. No $V_{1a}$ antagonist activity is reported. European Patent Application EP 1 449 844 A1, published 25 Aug. 2004, discloses a number of compounds which are claimed to be $V_{1a}$ antagonists and to find use in the treatment of primary dysmenorrhoea.

In the manufacture of pharmaceutical formulations, it is important that the active compound is in a form in which it can be conveniently handled and processed in order to obtain a commercially viable manufacturing process. Accordingly, the chemical stability and the physical stability of the active compound are important factors. The active compound, and formulations containing it, must be capable of being effectively stored over appreciable periods of time, without exhibiting any significant change in the physico-chemical characteristics (e.g. chemical composition, density, hygroscopicity and solubility) of the active compound.

Furthermore, if the active compound is to be incorporated into a dosage form for oral administration, such as a tablet, it is desirable that the active compound be readily micronised to yield a powder with good flow properties to aid manufacture. Moreover, it is desirable that the active compound be soluble to allow for faster and increased absorption of the active compound following administration.

It is known that manufacturing a particular physical form (or polymorph), such as a salt form, of a pharmaceutical ingredient can affect many aspects of its solid state properties and may offer advantages in aspects of solubility, dissolution rate, chemical stability, mechanical properties, technical feasibility, processability, pharmacokinetics and bioavailability. Some of these are described in "Handbook of Pharmaceutical Salts; Properties, Selection and Use", P. Heinrich Stahl, Camille G. Wermuth (Eds.) (Verlag Helvetica Chimica Acta, Zurich). Methods of manufacturing solid-state forms are described in "Practical Process Research and Development", Neal G. Anderson (Academic Press, San Diego) and "Polymorphism: In the Pharmaceutical Industry", Rolf Hilfiker (Ed) (Wiley VCH). Polymorphism in pharmaceutical crystals is described in Byrn (Byrn, S. R., Pfeiffer, R. R., Stowell, J. G., "Solid-State Chemistry of Drugs", SSCI Inc., West Lafayette, Ind., 1999), Brittain, H. G., "Polymorphism in Pharmaceutical Solids", Marcel Dekker, Inc., New York, Basel, 1999) or Bernstein (Bernstein, J., "Polymorphism in Molecular Crystals", Oxford University Press, 2002).

International Patent Application WO 2006/021213 (PCT/DK2005/000540) describes a novel class of vasopressin antagonists that display high, selective potency at the $V_{1a}$ receptor. One such vasopressin antagonist described in PCT/DK2005/000540 is cyclopropanecarboxylic acid 4-(6-chloro-3-methyl-4,10-dihydro-3H-2,3,4,9-tetraazabenzo[f]azulene-9-carbonyl)-2-fluoro-benzylamide. The preparation of cyclopropanecarboxylic acid 4-(6-chloro-3-methyl-4,10-dihydro-3H-2,3,4,9-tetraazabenzo[f]azulene-9-carbonyl)-2-fluoro-benzylamide described in PCT/DK2005/000540 yields a solid which is poorly soluble and thus less suitable for oral administration. It has now been found possible to prepare a salt of cyclopropanecarboxylic acid 4-(6-chloro-3-methyl-4,10-dihydro-3H-2,3,4,9-tetraazabenzo[f]azulene-9-carbonyl)-2-fluoro-benzylamide, which has unexpectedly advantageous physico-chemical properties and which may be suitable for use in a formulation for oral administration. In particular, the salt form of the present invention was unexpectedly found to be 8× more soluble in water than known free base of cyclopropanecarboxylic acid 4-(6-chloro-3-methyl-4,10-dihydro-3H-2,3,4,9-tetraazabenzo[f]azulene-9-carbonyl)-2-fluoro-benzylamide. Moreover, when tested in a rat model of oral availability, significant improvements in plasma exposure were observed following dosing with the salt of the present invention. In contrast, the known free base was only minimally absorbed when tested in the same model.

Thus, in accordance with the present invention, there is provided a salt which is a tosylate (para-toluenesulphonate) salt of cyclopropanecarboxylic acid 4-(6-chloro-3-methyl-4,10-dihydro-3H-2,3,4,9-tetraazabenzo[f]azulene-9-carbonyl)-2-fluoro-benzylamide. In the present application this salt may be referred to as the 'tosylate salt'.

The salt of the present invention is herein referred to as cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate. The name cyclopropanecarboxylic acid 4-(6-chloro-3-methyl-4,10-dihydro-3H-2,3,4,9-tetraazabenzo[f]azulene-9-carbonyl)-2-fluoro-benzylamide denotes the structure depicted in FIG. A.

Figure A

The present invention encompasses solvates (e.g. hydrates) of the tosylate salt.

Seven different physical forms of the tosylate salt of the present invention have been isolated and characterised to date (Form 1, Form 2, Form 3, Form 4, Form 5, Form 6 and Form 7). All seven are forms of the tosylate salt, i.e. cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate.

In the present specification, X-ray powder diffraction peaks (expressed in degrees 2θ) are measured using copper X-rays with a wavelength of 1.5406 Å (alpha1) and 1.5444 Å (alpha2).

Thus, the present invention also provides a physical form (Form 1) of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, which exhibits at least the following characteristic X-ray powder diffraction peaks (Cu Kα radiation, expressed in degrees 2θ) at approximately:
(1) 8.2, 21.4, 23.3 and 25.8, or
(2) 8.2, 12.2, 21.4, 23.3 and 25.8, or
(3) 8.2, 12.2, 17.2, 21.4, 23.3 and 25.8

The term "approximately" means in this context that there is an uncertainty in the measurements of the degrees 2θ of 0.2 (expressed in degrees 2θ).

The present invention also provides a physical form (Form 1) of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, having an X-ray powder diffraction pattern comprising specific peaks (expressed in degrees 2θ) at approximately 8.2, 12.2, 17.2, 20.4, 21.4, 23.3, 25.8 and 27.4.

The present invention also provides a physical form (Form 1) of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, having an X ray powder diffraction pattern which exhibits at least the following characteristic d-space values (Å) of approximately:
(1) 10.73, 4.15, 3.65 and 3.44, or
(2) 10.73, 7.25, 4.15, 3.65 and 3.44, or
(3) 10.73, 7.25, 5.17, 4.15, 3.65 and 3.44

Figure 1:
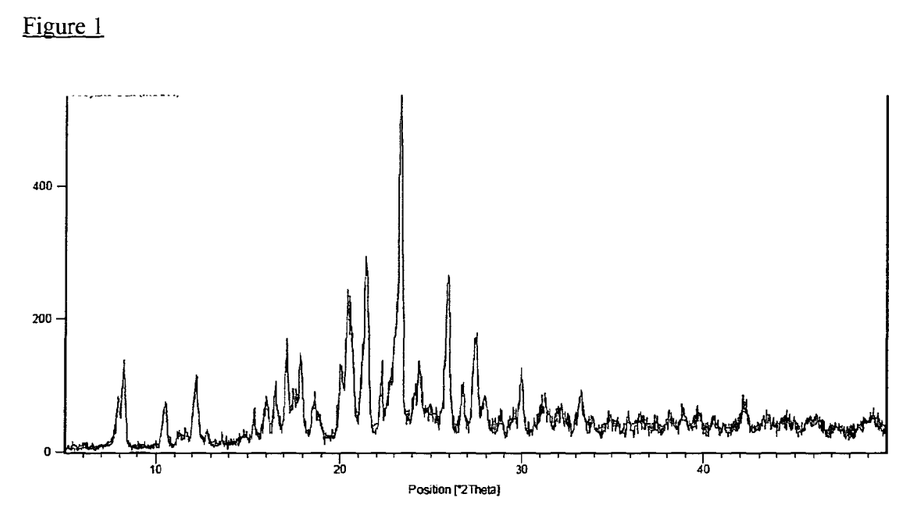
FIG. 1: X-ray powder diffraction pattern of physical Form 1 of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate.

FIG. 1 shows an X-ray powder diffraction pattern of physical Form 1 of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate. The present invention also provides a salt form having an X-ray powder diffraction pattern substantially the same as that shown in FIG. 1.

Figure 10:
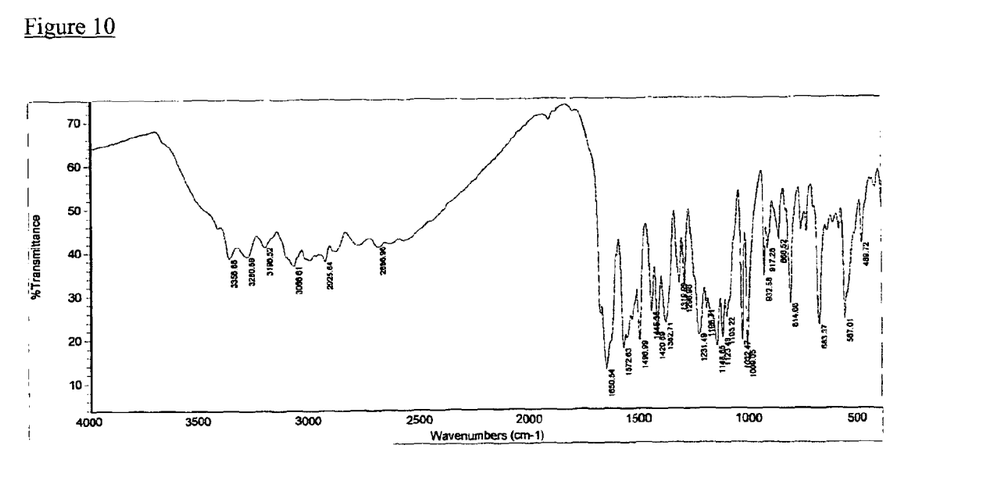
FIG. 10: Infra-red spectrum of physical Form 1 of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate.

FIG. 10 shows an IR spectrum of Form 1 of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate. Accordingly, the present invention provides a provides a salt form which is characterised by an IR spectrum having characteristic peaks expressed in $cm^{-1}$ at approximately 3359, 3281, 3197, 3067, 2926, approx. 1682 (shoulder), 1651, 1573, 1033 and 1009. The term "approximately" means in this context that the $cm^{-1}$ values can vary, e.g. by up to ±1 $cm^{-1}$. Additionally, the present invention provides a salt form having an IR spectrum substantially the same as that shown in FIG. 10.

The present invention also provides a physical form (Form 2) of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, which exhibits at least the following characteristic X-ray powder diffraction peaks (Cu Kα radiation, expressed in degrees 2θ) at approximately:
(1) 7.9, 16.4, 19.3, and 25.1, or
(2) 7.9, 16.4, 19.3, 21.6 and 25.1, or
(3) 7.9, 16.4, 17.8, 19.3, 21.6 and 25.1.

The present invention also provides a physical form (Form 2) of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, having an X ray powder diffraction pattern comprising specific peaks (expressed in degrees 2θ) at approximately 7.9, 11.7, 16.4, 17.6, 17.8, 19.3, 21.6 and 25.1.

The present invention also provides a physical form (Form 2) of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, having an X ray powder diffraction pattern which exhibits at least the following characteristic d-space values (Å) of approximately:
(1) 11.22, 5.39, 4.59, and 3.55, or
(2) 11.22, 5.39, 4.59, 4.11 and 3.55, or
(3) 11.22, 5.39, 4.98, 4.59, 4.11 and 3.55.

Figure 2:
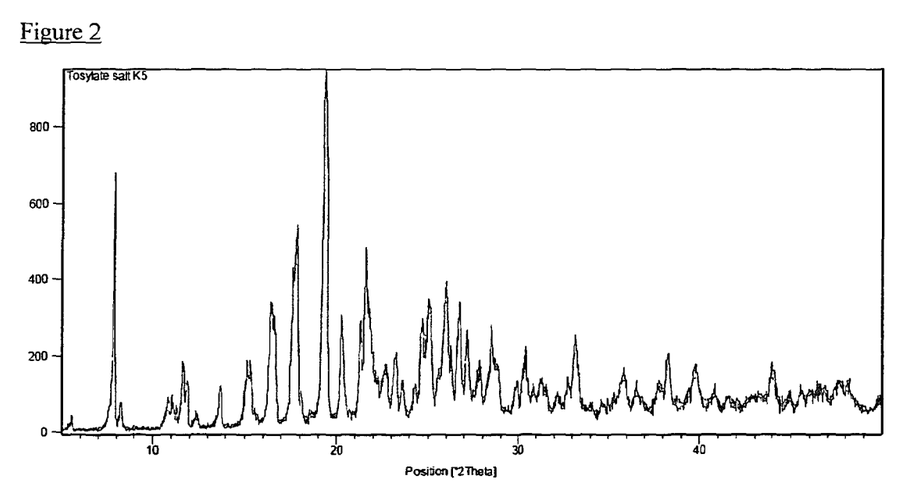
FIG. 2: X-ray powder diffraction pattern of physical Form 2 of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate.

FIG. 2 shows an X-ray powder diffraction pattern of physical Form 2 of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate. The present invention also provides a salt form having an X-ray powder diffraction pattern substantially the same as that shown in FIG. 2.

The present invention also provides a physical form (Form 3) of cyclopropanecarboxylic acid 4-(6-chloro-3-methyl-4,10-dihydro-3H-2,3,4,9-tetraazabenzo azulene-9-carbonyl)-2-fluoro-benzylamide para-toluenesulphonate, which exhibits at least the following characteristic X-ray powder diffraction peaks (Cu Kα radiation, expressed in degrees 2θ) at approximately:
(1) 7.7, 18.6, 24.9 and 25.0, or
(2) 7.7, 18.6, 20.4, 24.9 and 25.0, or
(3) 7.7, 15.8, 18.6, 20.4, 24.9 and 25.0.

The present invention also provides a physical form (Form 3) of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, having an X ray powder diffraction pattern comprising specific peaks (expressed in degrees 2θ) at approximately 7.7, 11.9, 15.8, 17.6, 18.6, 20.4, 21.0, 23.1, 24.9 and 25.0.

The present invention also provides a physical form (Form 3) of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, having an X ray powder diffraction pattern which exhibits at least the following characteristic d-space values (Å) of approximately:
(1) 11.52, 4.78, 3.57 and 3.55, or
(2) 11.52, 4.78, 4.36, 3.57 and 3.55, or
(3) 11.52, 5.61, 4.78, 4.36, 3.57 and 3.55.

Figure 3:
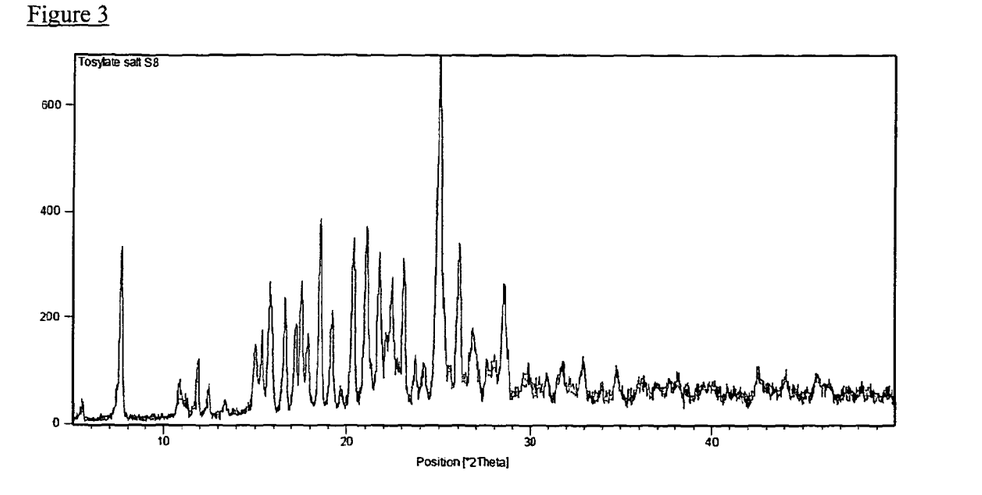
FIG. 3: X-ray powder diffraction pattern of physical Form 3 of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate.

FIG. 3 shows an X-ray powder diffraction pattern of physical Form 3 of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate. The present invention also provides a salt form having an X-ray powder diffraction pattern substantially the same as that shown in FIG. 3.

The present invention also provides a physical form (Form 4) of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, which exhibits at least the following characteristic X-ray powder diffraction peaks (Cu Kα radiation, expressed in degrees 2θ) at approximately:
(1) 10.8, 15.4, 18.8 and 24.9, or
(2) 10.8, 15.5, 18.8, 21.3 and 24.9, or
(3) 10.8, 15.5, 18.8, 21.3, 21.6 and 24.9.

The present invention also provides a physical form (Form 4) of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, having an X ray powder diffraction pattern comprising specific peaks (expressed in degrees 2θ) at approximately 7.8, 10.8, 15.5, 15.6, 17.8, 18.8, 19.3, 20.6, 21.3, 21.6 and 24.9.

The present invention also provides a physical form (Form 4) of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, having an X ray powder diffraction pattern which exhibits at least the following characteristic d-space values (Å) of approximately:
(1) 8.21, 5.73, 4.72 and 3.58, or
(2) 8.21, 5.73, 4.72, 4.18 and 3.58, or
(3) 8.21, 5.73, 4.72, 4.18, 4.10 and 3.58.

Figure 4:
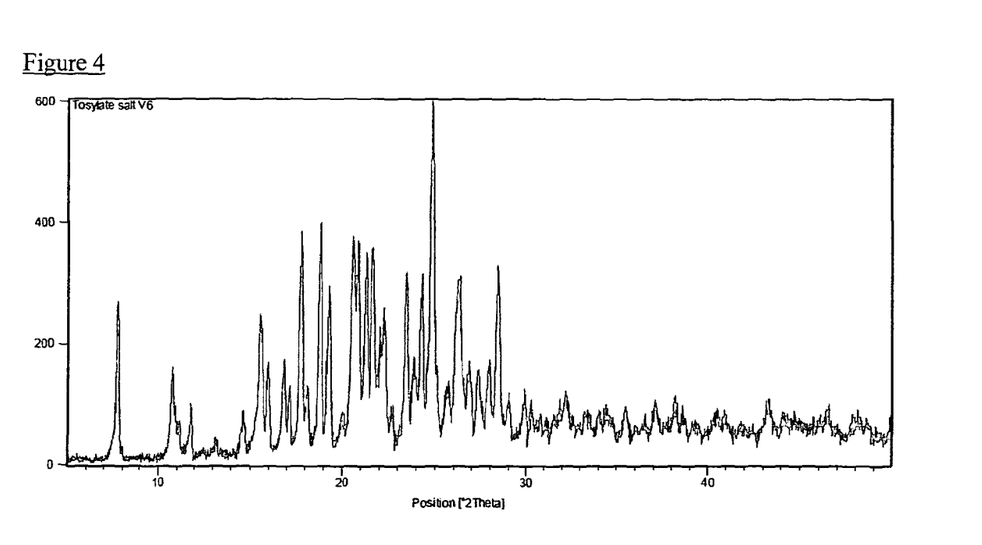
FIG. 4: X-ray powder diffraction pattern of physical Form 4 of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate.

FIG. 4 shows an X-ray powder diffraction pattern of physical Form 4 of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate. The present invention also provides a salt form having an X-ray powder diffraction pattern substantially the same as that shown in FIG. 4.

The present invention also provides a physical form (Form 5) of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, which exhibits at least the following characteristic X-ray powder diffraction peaks (Cu Kα radiation, expressed in degrees 2θ) at approximately:
(1) 17.8, 20.3, 23.2, and 28.5, or
(2) 7.7, 17.8, 20.3, 23.2, and 28.5, or
(3) 7.7, 17.8, 20.3, 23.2, 28.2 and 28.5.

The present invention also provides a physical form (Form 5) of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, having an X ray powder diffraction pattern comprising specific peaks (expressed in degrees 2θ) at approximately 7.7, 17.8, 18.8, 20.3, 21.0, 23.2, 24.5, 25.1, 28.2 and 28.5.

The present invention also provides a physical form (Form 5) of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, having an X ray powder diffraction pattern which exhibits at least the following characteristic d-space values (Å) of approximately:
(1) 4.99, 4.36, 3.84, and 3.13, or
(2) 11.43, 4.99, 4.36, 3.84, and 3.13, or
(3) 11.43, 4.99, 4.36, 3.84, 3.17 and 3.13.

Figure 5:
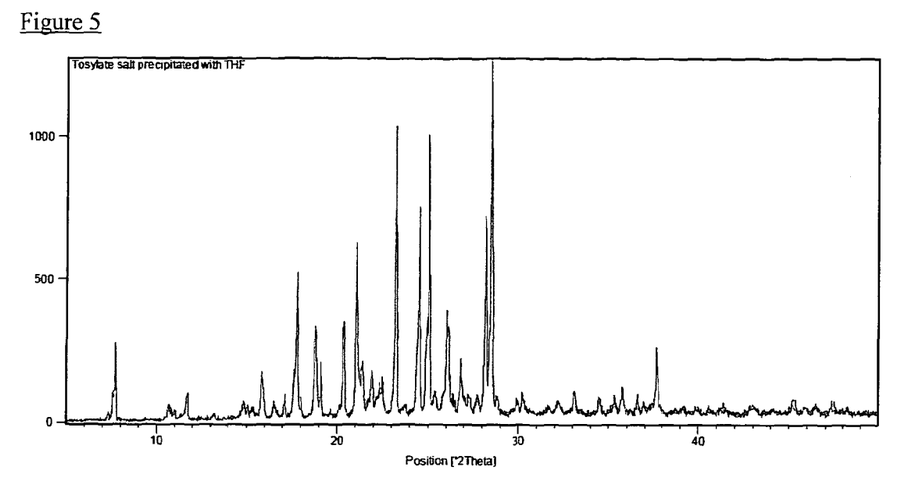
FIG. 5: X-ray powder diffraction pattern of physical Form 5 of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate.

FIG. 5 shows an X-ray powder diffraction pattern of physical Form 5 of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate. The present invention also provides a salt form having an X-ray powder diffraction pattern substantially the same as that shown in FIG. 5.

The present invention also provides a physical form (Form 6) of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, which exhibits at least the following characteristic X-ray powder diffraction peaks (Cu Kα radiation, expressed in degrees 2θ) at approximately:
(1) 15.5, 18.2, 21.6 and 25.9, or
(2) 15.5, 18.2, 20.1, 21.6 and 25.9, or
(3) 15.5, 18.2, 20.1, 20.8, 21.6 and 25.9.

The present invention also provides a physical form (Form 6) of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, having an X ray powder diffraction pattern comprising specific peaks (expressed in degrees 2θ) at approximately 7.5, 15.5, 18.2, 20.1, 20.8, 21.6, 27.3 and 25.9.

The present invention also provides a physical form (Form 6) of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, having an X ray powder diffraction pattern which exhibits at least the following characteristic d-space values (Å) of approximately:
(1) 5.71, 4.88, 4.12 and 3.44, or
(2) 5.71, 4.88, 4.42, 4.12 and 3.44, or
(3) 5.71, 4.88, 4.42, 4.27, 4.12 and 3.44.

Figure 6:
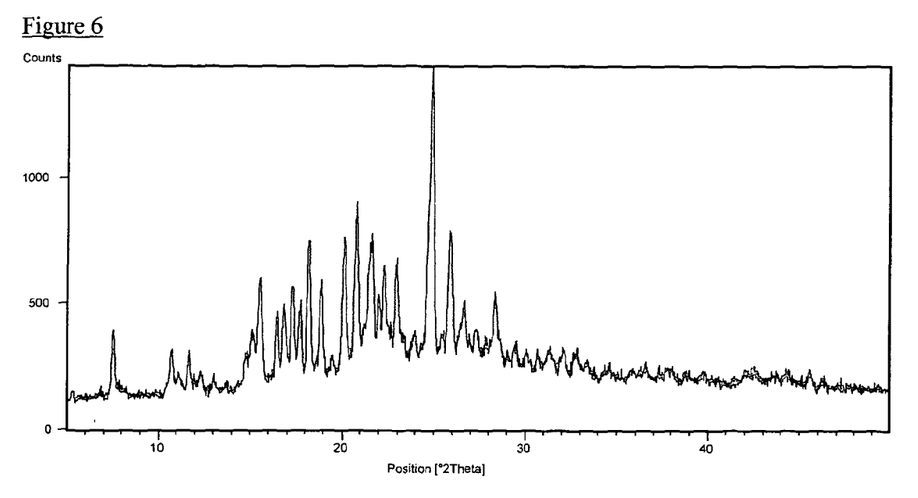
FIG. 6: X-ray powder diffraction pattern of physical Form 6 of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate.

FIG. 6 shows an X-ray powder diffraction pattern of physical Form 6 of cyclopropanecarboxylic acid 4-(6-chloro-3-methyl-4,10-dihydro-3H-2,3,4,9-tetraazabenzo azulene-9-carbonyl)-2-fluoro-benzylamide para-toluenesulphonate. The present invention also provides a salt form having an X-ray powder diffraction pattern substantially the same as that shown in FIG. 6.

Figure 11:
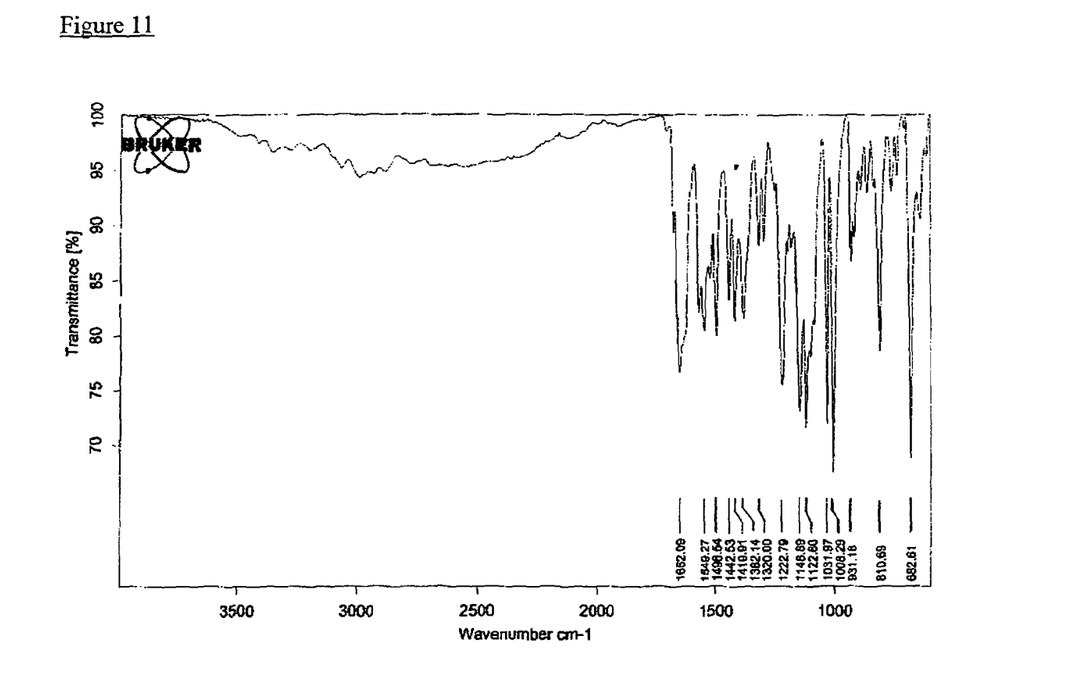
FIG. 11: Infra-red spectrum of physical Form 6 of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate.

FIG. 11 shows an IR spectrum of Form 6 of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate. Accordingly, the present invention provides a provides a salt form which is characterised by an IR spectrum having characteristic peaks expressed in cm$^{-1}$ at approximately 1653, 1549, 1497, 1443, 1420, 1382, 1320, 1223, 1149, 1123, 1032, 1008, 931, 811 and 683. The term "approximately" means in this context that the cm$^{-1}$ values can vary, e.g. by up to ±1 cm$^-$. Additionally, the present invention provides a salt form having an IR spectrum substantially the same as that shown in FIG. 11.

The present invention also provides a physical form (Form 7) of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, which exhibits at least the following characteristic X-ray powder diffraction peaks (Cu Kα radiation, expressed in degrees 2θ) at approximately:
(1) 7.9, 15.8, 21.6 and 32.7, or
(2) 7.9, 15.8, 21.6, 23.5 and 32.7, or
(3) 7.9, 15.8, 20.1, 21.6, 23.5 and 32.7.

The present invention also provides a physical form (Form 7) of cyclopropanecarboxylic acid 4-(6-chloro-3-methyl-4,10-dihydro-3H-2,3,4,9-tetraazabenzo azulene-9-carbonyl)-2-fluoro-benzylamide para-toluenesulphonate, having an X ray powder diffraction pattern comprising specific peaks (expressed in degrees 2θ) at approximately 7.9, 15.8, 19.9, 20.1, 20.7, 21.3, 21.6, 23.2, 23.5, 27.0 and 32.7.

The present invention also provides a physical form (Form 7) of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, having an X ray powder diffraction pattern which exhibits at least the following characteristic d-space values (Å) of approximately:
(1) 11.26, 5.60, 4.11 and 2.74, or
(2) 11.26, 5.60, 4.11, 3.78 and 2.74, or
(3) 11.26, 5.60, 4.41, 4.11, 3.78 and 2.74.

Figure 7:
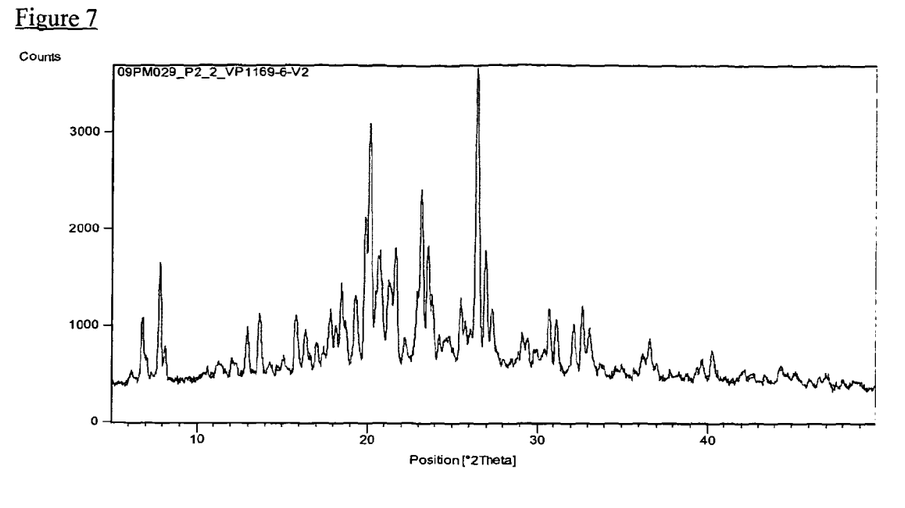
FIG. 7: X-ray powder diffraction pattern of physical Form 7 of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate.

FIG. 7 shows an X-ray powder diffraction pattern of physical Form 7 of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate. The present invention also provides a salt form having an X-ray powder diffraction pattern substantially the same as that shown in FIG. 7.

Figure 12:
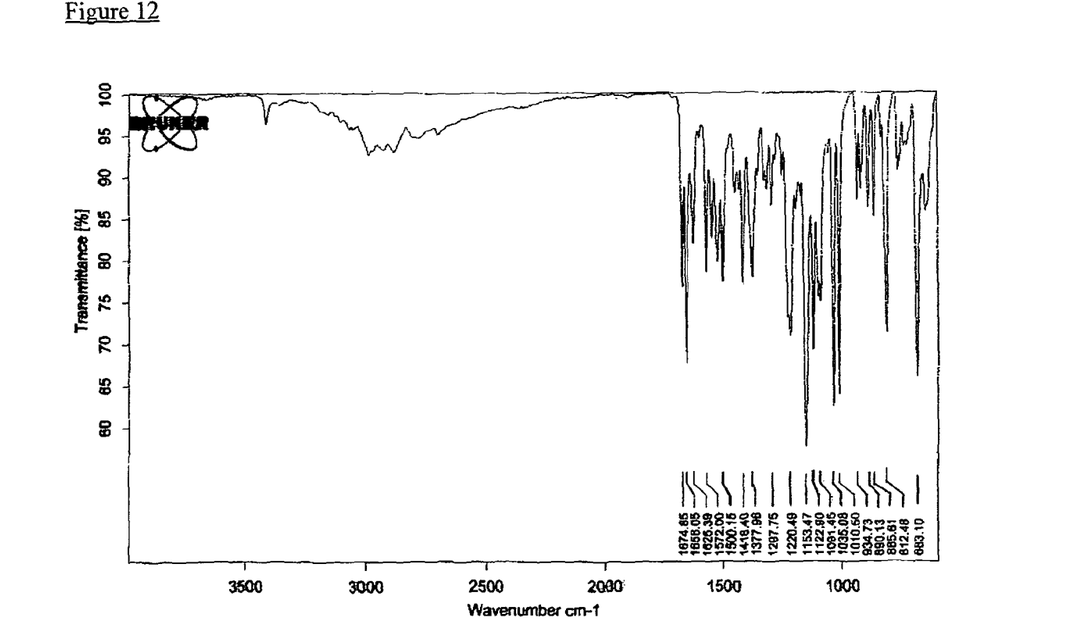
FIG. 12: Infra-red spectrum of physical Form 7 of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate.

FIG. 12 shows an IR spectrum of Form 7 of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate. Accordingly, the present invention provides a provides a salt form which is characterised by an IR spectrum having characteristic peaks expressed in cm$^{-1}$ at approximately 1675, 1656, 1625, 1572, 1500, 1418, 1378, 1298, 1221, 1154, 1123, 1092, 1035, 1011, 935, 890, 866, 813 and 683. The term "approximately" means in this context that the cm$^{-1}$ values can vary, e.g. by up to ±1 cm$^{-1}$. Additionally, the present invention provides a salt form having an IR spectrum substantially the same as that shown in FIG. 12.

The tosylate salt of the present invention can exist in both unsolvated and solvated forms. The term 'solvate' is used herein to describe a molecular complex comprising the compound of the invention and an amount of one or more pharmaceutically acceptable solvents, for example, ethanol. The term 'hydrate' is employed when the solvent is water.

The tosylate salt of the present invention may be prepared as follows: A mixture of cyclopropanecarboxylic acid 4-(6-chloro-3-methyl-4,10-dihydro-3H-2,3,4,9-tetraazabenzo[f] azulene-9-carbonyl)-2-fluoro-benzylamide (prepared by the method described in PCT/DK2005/000540) and para-toluenesulphonic acid are combined in a suitable solvent (e.g. methanol) and stirred at a suitable temperature (e.g. 20 to 25° C.) for a period of time (e.g. 6 to 24 hours). The solvent is then removed (e.g. by rotary evaporation). The dried material may then be suspended in a suitable solvent (e.g. t-butyl methyl ether) and then sonicated for a suitable time (e.g. 2 to 6 hours) at a suitable temperature (e.g. 50 to 70° C.). The solids may then be collected (e.g. by centrifugation) and dried under vacuum to yield cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate in amorphous form.

Physical Form 1 may, for example, be prepared by heating the amorphous form, prepared as described above, in acetone with stirring at approx. 60° C. for approx. 90 minutes. The solids may then be collected (e.g. by centrifugation) and dried under vacuum to yield physical Form 1.

Alternatively, physical Form 1 may be prepared by adding acetonitrile and ethyl acetate to a solution of the amorphous form in toluene/isobutanol, cooling the mixture and then seeding it with crystals of physical Form 1. After further cooling and stirring, the solids were isolated by filtration, washed with ethyl acetate and then dried to yield physical Form 1.

As previously mentioned, the tosylate salt of the present invention has a number of therapeutic applications, particularly in the treatment of diseases or conditions mediated by vasopressin $V_{1a}$.

Accordingly, the present invention provides cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, or a pharmaceutically acceptable solvate thereof, as hereinbefore defined, for use in therapy.

The present invention also provides for the use of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, or a pharmaceutically acceptable solvate thereof, as hereinbefore defined, in the manufacture of a medicament for the treatment of a disease or condition mediated by vasopressin $V_{1a}$ receptors.

The present invention also provides cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, or a pharmaceutically acceptable solvate thereof, as hereinbefore defined, for use in the treatment of a disease or condition mediated by vasopressin $V_{1a}$ receptors.

The present invention also provides a method of treatment of a disease or condition mediated by vasopressin $V_{1a}$ receptors, said method comprising administering to a mammal in need of such treatment a therapeutically effective amount of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, or a pharmaceutically acceptable solvate thereof, as hereinbefore defined.

In an aspect, the disease or condition mediated by vasopressin $V_{1a}$ receptors is selected from dysmenorrhoea (primary dysmenorrhoea and/or secondary dysmenorrhoea), preterm labour, hypertension, Raynaud's disease, brain oedema, motion sickness, hyperlipemia, small cell lung cancer, depression, anxiety, hyponatremia, liver cirrhosis and congestive heart failure.

In an aspect, the disease or condition mediated by vasopressin $V_{1a}$ receptors is dysmenorrhoea (primary dysmenorrhoea and/or secondary dysmenorrhoea).

In the context of the present invention, references herein to "treatment" include references to curative, palliative and prophylactic treatment, unless there are specific indications to the contrary. The terms "therapy, "therapeutic" and "therapeutically" should be construed in the same way.

The tosylate salt of the present invention may be administered alone or in combination with one or more other drugs. Generally, it will be administered as a formulation in association with one or more pharmaceutically acceptable excipients. The term "excipient" is used herein to describe any ingredient other than the compound(s) of the invention which may impart either a functional (i.e., drug release rate controlling) and/or a non-functional (i.e., processing aid or diluent) characteristic to the formulations. The choice of excipient will to a large extent depend on factors such as the particular mode of administration, the effect of the excipient on solubility and stability, and the nature of the dosage form.

Pharmaceutical compositions suitable for the delivery of the tosylate salt of the present invention and methods for their preparation will be readily apparent to those skilled in the art. Such compositions and methods for their preparation may be found, for example, in Remington's Pharmaceutical Sciences, 19th Edition (Mack Publishing Company, 1995).

For administration to human patients, the total daily dose of the tosylate salt of the invention is typically in the range 0.01 mg and 1000 mg, or between 0.1 mg and 250 mg, or between 1 mg and 50 mg depending, of course, on the mode of administration. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

Accordingly, the present invention provides a pharmaceutical composition comprising cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, or a pharmaceutically acceptable solvate thereof, as hereinbefore defined, and a pharmaceutically acceptable carrier, diluent or excipient.

The pharmaceutical compositions may be administered topically (e.g. to the skin or to the lung and/or airways) in the form, e.g., of creams, solutions, suspensions, heptafluoroalkane (HFA) aerosols and dry powder formulations; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

In an embodiment of the invention, the active ingredient is administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids, emulsions or powders; lozenges (including liquid-filled); chews; gels; fast dispersing dosage forms; films; ovules; sprays; and buccal/mucoadhesive patches.

Formulations suitable for oral administration may also be designed to deliver the tosylate salt in an immediate release manner or in a rate-sustaining manner, wherein the release profile can be delayed, pulsed, controlled, sustained, or delayed and sustained or modified in such a manner which optimises the therapeutic efficacy of the said tosylate salt. Means to deliver compounds in a rate-sustaining manner are known in the art and include slow release polymers that can be formulated with the said compounds to control their release.

Examples of rate-sustaining polymers include degradable and non-degradable polymers that can be used to release the said compounds by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

Liquid (including multiple phases and dispersed systems) formulations include emulsions, suspensions, solutions, syrups and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The tosylate salt of the invention may also be used in fast-dissolving, fast-disintegrating dosage forms such as those described in Liang and Chen, Expert Opinion in Therapeutic Patents, 2001, 11 (6), 981-986.

The formulation of tablets is discussed in Pharmaceutical Dosage Forms: Tablets, Vol. 1, by H. Lieberman and L. Lachman (Marcel Dekker, New York, 1980).

The invention will now be illustrated by the following non-limiting Examples. In the Examples the following Figures are presented.

GENERAL EXPERIMENTAL DETAILS

All reactions were carried out under an atmosphere of nitrogen unless specified otherwise. All solvents and commercial reagents were used as received.

$^1$H NMR spectra were recorded on a Jeol EX 270 (270 MHz) or Brucker Avance III (400 MHz) spectrometer with reference to deuterium solvent (CDCl$_3$ unless otherwise stated) and at RT. Molecular ions were obtained using LCMS which was carried out using a Chromolith Speedrod RP-18e column, 50×4.6 mm, with a linear gradient 10% to 90% 0.1% HCO$_2$H/MeCN into 0.1% HCO$_2$H/H$_2$O over 11 min, flow rate 1.5 mL/min. Data was collected using a Thermofinnigan Surveyor MSQ mass spectrometer with electospray ionisation in conjunction with a Thermofinnigan Surveyor LC system.

Chemical names were generated using the Autonom software provided as part of the ISIS Draw package from MDL Information Systems.

Two methods for measuring differential scanning calorimetry (DSC) thermograms were used:—
1) Using a Perkin-Elmer Diamond Differential Scanning calorimeter (equipped with a liquid-nitrogen cooling unit), with aluminium pans and non-hermetic lids. The sample weights varied between 1-2 mg. The procedure was carried out under a flow of helium gas (20 ml/min) and the temperature studied from 20 to 300° C. at a constant rate of temperature increase of 200° C. per minute. Prior to analysis the instrument was temperature and heat-flow calibrated using an indium reference standard.
2) Using a Mettler DSC 12E model with external cooling using a Julabo F 25 circulating bath. The samples are weighed into aluminium crucibles and then sealed with a pin pricked lid. A heating rate of 10° C. per minute was applied and an empty sealed DSC pan was used as the reference.

Two methods of measuring infra-red spectra were used:—
1) Using a Thermo Nicolet Avatar FT-IR spectrometer with Omnic data processing software. A sample of approximately 3 mg was triturated with 300 mg potassium bromide and compressed under vacuum into a pellet on a hydraulic press. The spectrum of the pellet was recorded in the infrared region of the spectrum between 400 cm$^{-1}$ and 4000 cm$^{-1}$.
2) Using a Bruker Tensor 27. The spectrum between 550 cm$^{-1}$ and 4000 cm$^{-1}$ is recorded.

Ultra-violet spectra were obtained with solutions of test samples in acetonitrile (Far UV grade—190 nm cut-off) using a SpectroMax UV spectrophotometer in quartz cuvettes. A spectrum was generated over 200-600 nm with 1 nm increments at 25° C. The spectrum obtained from the analysis of the cuvette filled with blank acetonitrile was subtracted from that of the test sample.

Accurate mass determination was performed on a Waters LCT premier time of flight (TOF) mass spectrometer, optimised for resolution in W mode positive ion electrospray before a calibration with sodium formate was performed. A solution of reserpine and nifedipine was prepared and infused into the ion source to give molecular ions of between 100 and 250 CPS and a mass spectrum was acquired for 2 minutes in MCA mode. A solution of test sample was then introduced into this flow at a flow-rate and concentration suitable to produce a molecular ion in the same intensity range as the two calibrant ions. Data was acquired for 2 minutes in MCA mode.

X-Ray Powder Diffraction (XRPD) patterns were collected using sample weights of approximately 2-10 mg, which was gently compressed on the XRPD zero background single obliquely cut silica sample holder. The sample was then loaded into a Philips X-Pert MPD diffractometer or a Philips X-Pert PRO diffractometer and analysed using the following experimental conditions:—
Tube anode: Cu
Generator tension: 40 kV
Tube current: 40 mA
Wavelength alpha1: 1.5406 Å
Wavelength alpha2: 1.5444 Å
Start angle [2 θ]: 5
End angle [2 θ]: 50
Time per step: 2.5 seconds (X-Pert MPD) or 31 seconds (X-Pert Pro)

Cyclopropanecarboxylic acid 4-(6-chloro-3-methyl-4,10-dihydro-3H-2,3,4,9-tetraazabenzo[f]azulene-9-carbonyl)-2-fluoro-benzylamide (Free Base)

The title compound may be prepared by the method described in PCT/DK2005/000540.

The product arising from the method described in PCT/DK2005/000540 may be recrystallised. The title compound (19.75 g, 43.5 mmol) was taken up in refluxing ethanol (250 mL). To the solution was added hot water (500 mL). The solution was allowed to cool slowly without stirring and left to stand at room temperature for 3 days. The resultant suspension was then stirred in an ice bath for 1 hour and the precipitate collected by vacuum filtration. The solid was dried at 55° C. for 6 hours. It was dried further at room temperature in vacuo for 16 hours. Finally it was dried for 24 hours at room temperature, in vacuo, over phosphorous pentoxide to afford fine white needles (yield 18.49 g, 94%).

Melting point (capillary tube) 235-237° C.

Melting point approximately 235° C. (DSC Method 1, onset temperature)

$^1$H NMR (270 MHz, d$_6$ DMSO) δ 0.65-0.67 (4H, m), 1.53-1.62 (1H, m), 3.77 (3H, s), 3.93 (1H, d, J=14.6 Hz), 4.23 (2H, d, J=5.4 Hz), 5.62 (1H, d, J=14.6 Hz), 6.71 (1H, d, J=8.4 Hz), 6.84 (1H, d, J=8.4 Hz), 6.92-6.96 (2H, m), 7.09-7.15 (1H, m), 7.20 (1H, s), 7.37 (1H, s), 8.52 (1H, t, J=5.4 Hz), 8.80 (1H, s) ppm.

Figure 8:
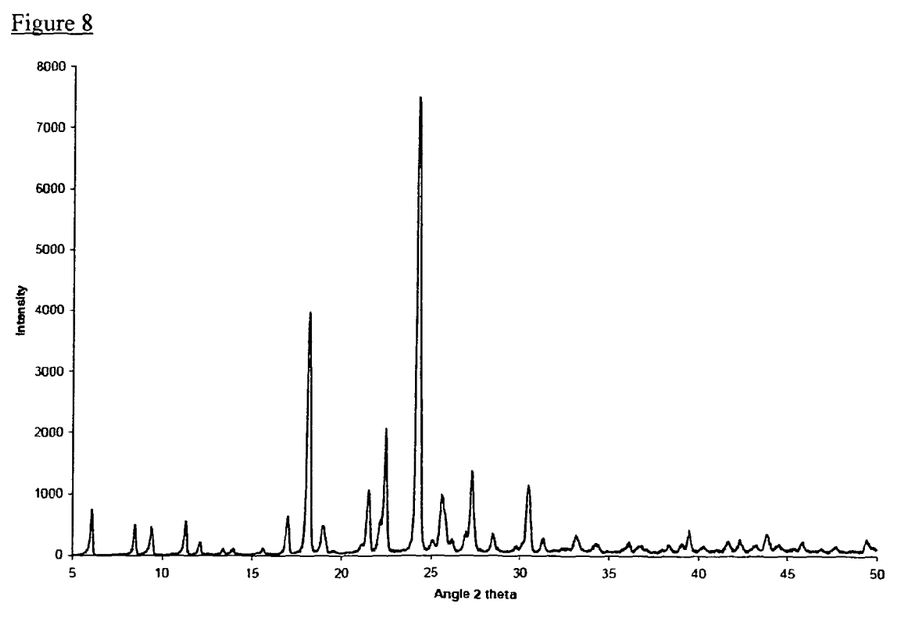
FIG. 8: X-ray powder diffraction pattern of cyclopropanecarboxylic acid 4-(6-chloro-3-methyl-4,10-dihydro-3H-2,3,4,9-tetraazabenzo[f]azulene-9-carbonyl)-2-fluoro-benzylamide.

An XRPD diffractogram of cyclopropanecarboxylic acid 4-(6-chloro-3-methyl-4,10-dihydro-3H-2,3,4,9-tetraazabenzo[f]azulene-9-carbonyl)-2-fluoro-benzylamide is shown in FIG. 8.

Cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate 2.50 g of cyclopropanecarboxylic acid 4-(6-chloro-3-methyl-4,10-dihydro-3H-2,3,4,9-tetraazabenzo[f]azulene-9-carbonyl)-2-fluoro-benzylamide (5.52 mmol) was dissolved in 20 mL of methanol along with 6.4 mL (5.79 mmol) of 0.905M para-toluenesulphonic acid. The solution was stirred and the methanol removed by rotary evaporation. The dry material was suspended in 20 mL of t-butyl methyl ether and sonicated at 60° C. for 4 hours. The sample was centrifuged to separate the solid material from the supernatant and the solid material was dried under vacuum. The sample of tosylate salt so obtained is hereinafter referred to as the amorphous form.
Physical Form 1
Amorphous form (as prepared herein above) was stirred in acetone (100 mL) at 60° C. for 90 minutes. The sample was centrifuged to separate the solid material from the supernatant and the solid material was dried under vacuum. Successful salt formation was confirmed by XRPD and microanalysis.
Microanalysis (1); C 57.37%, H 4.37%, N 11.29%
Microanalysis (2); C 57.48%, H 4.54%, N 11.32%
(Theoretical; C 57.55%, H 4.67%, 11.19%)
Melting point 204° C. (DSC Method 1, onset temperature)
An XRPD spectrum of Form 1 is presented in FIG. 1.

Peak position table: -

| Pos. [°2Th.] | Height [cts] | FWHM [°2Th.] | d-spacing [Å] | Rel. Int. [%] |
|---|---|---|---|---|
| 6.1161 | 3.34 | 0.2362 | 14.43917 | 0.97 |
| 7.943 | 47.11 | 0.0787 | 11.12174 | 13.71 |
| 8.2299 | 88.19 | 0.0984 | 10.73471 | 25.67 |
| 9.3698 | 3.05 | 0.0984 | 9.43122 | 0.89 |
| 10.5529 | 34.27 | 0.0787 | 8.37633 | 9.98 |
| 11.2676 | 11.95 | 0.1968 | 7.84657 | 3.48 |
| 12.1963 | 55.78 | 0.2755 | 7.25109 | 16.23 |
| 12.766 | 13.36 | 0.1574 | 6.92879 | 3.89 |
| 13.6021 | 10.43 | 0.059 | 6.50467 | 3.04 |
| 14.8254 | 6.53 | 0.1968 | 5.97061 | 1.9 |
| 15.3878 | 25.92 | 0.0984 | 5.75362 | 7.54 |
| 15.994 | 34.13 | 0.1968 | 5.5369 | 9.93 |
| 16.4933 | 44.2 | 0.059 | 5.37039 | 12.86 |
| 17.042 | 70.38 | 0.059 | 5.19868 | 20.48 |
| 17.1468 | 97.28 | 0.059 | 5.16715 | 28.31 |
| 17.8394 | 82.75 | 0.059 | 4.96806 | 24.08 |
| 18.603 | 38.25 | 0.1574 | 4.76582 | 11.13 |
| 20.017 | 66.67 | 0.059 | 4.43225 | 19.4 |
| 20.3803 | 138.83 | 0.059 | 4.35405 | 40.41 |
| 20.6727 | 85.98 | 0.0787 | 4.29312 | 25.02 |
| 21.3778 | 157.97 | 0.0984 | 4.15308 | 45.98 |
| 22.286 | 47.1 | 0.0984 | 3.98585 | 13.71 |
| 23.2746 | 343.58 | 0.2165 | 3.81874 | 100 |
| 24.3462 | 51.85 | 0.0984 | 3.65303 | 15.09 |
| 24.9376 | 18.38 | 0.1574 | 3.56772 | 5.35 |
| 25.8448 | 133.7 | 0.096 | 3.4445 | 38.91 |
| 25.9441 | 116.19 | 0.0984 | 3.43155 | 33.82 |
| 26.6827 | 42.7 | 0.0984 | 3.33821 | 12.43 |
| 27.4416 | 98.17 | 0.059 | 3.24759 | 28.57 |
| 27.927 | 30.81 | 0.2362 | 3.19224 | 8.97 |
| 28.7954 | 11.42 | 0.2362 | 3.09791 | 3.32 |
| 29.3851 | 9.39 | 0.1574 | 3.03707 | 2.73 |
| 29.9507 | 55.11 | 0.2362 | 2.981 | 16.04 |
| 31.1679 | 24.04 | 0.3149 | 2.86729 | 7 |
| 32.0789 | 20.95 | 0.3149 | 2.78792 | 6.1 |
| 33.2414 | 38.6 | 0.1968 | 2.69302 | 11.24 |
| 33.8327 | 11.92 | 0.2362 | 2.6473 | 3.47 |
| 34.83 | 13.75 | 0.1968 | 2.57375 | 4 |
| 35.8516 | 13.35 | 0.1181 | 2.50272 | 3.88 |
| 36.4467 | 11.9 | 0.3149 | 2.46321 | 3.46 |
| 37.3372 | 7.44 | 0.1968 | 2.40648 | 2.16 |
| 38.0824 | 13.03 | 0.3149 | 2.36109 | 3.79 |
| 38.8091 | 15.76 | 0.2755 | 2.31853 | 4.59 |
| 39.6495 | 17.75 | 0.2362 | 2.2713 | 5.17 |
| 40.5044 | 11.09 | 0.3149 | 2.22531 | 3.23 |
| 42.0942 | 34.92 | 0.0787 | 2.14487 | 10.16 |
| 43.3899 | 13.1 | 0.3936 | 2.08378 | 3.81 |
| 44.4489 | 12.18 | 0.6298 | 2.03656 | 3.54 |
| 45.9299 | 11.9 | 0.7872 | 1.97428 | 3.46 |
| 47.2866 | 6.07 | 0.6298 | 1.92075 | 1.77 |
| 49.1985 | 13.44 | 0.384 | 1.85049 | 3.91 |

Further quantities of Form 1 were prepared as follows:
A solution of para-toluenesulfonic acid monohydrate in iso-butanol was added to a solution of cyclopropanecarboxylic acid 4-(6-chloro-3-methyl-4,10-dihydro-3H-2,3,4,9-tetraazabenzo[f]azulene-9-carbonyl)-2-fluoro-benzylamide in toluene/iso-butanol. Acetonitrile and ethyl acetate were added. The solution was allowed to cool and seeded with crystals of the title compound (as prepared herein above). After further cooling and stirring, the product was isolated by filtration, washed with ethyl acetate and then dried.

$^1$H NMR (400 MHz, $d_6$ DMSO (80 mg/mL)) δ 0.63-0.65 (4H, m), 1.60-1.66 (1H, m), 2.32 (3H, s), 3.92 (3H, s), 4.02 (1H, d, J=14.5 Hz), 4.26 (2H, d, J=5.8 Hz), 5.72 (1H, d, J=14.5 Hz), 6.86 (1H, dd, J=2.1, 8.5 Hz), 6.94 (1H, d, J=8.5 Hz), 7.00-7.04 (2H, m), 7.14-7.18 (3H, m), 7.48 (1H, d, J=2.1 Hz), 7.55 (2H, d, J=8.0 Hz), 7.86 (1H, s), 8.56 (1H, t, J=5.8 Hz), 9.45 (1H, s), 10.71 (1H, brs) ppm.

$^{13}$C NMR (400 MHz, $d_6$ DMSO (80 mg/mL)) δ 6.35, 13.42, 20.64, 35.00, 35.53, 42.34, 102.78, 114.09, 119.72, 122.01, 123.35, 125.42, 127.92, 128.16, 128.79, 131.28, 131.94, 132.42, 133.11, 136.24, 138.04, 141.72, 144.96, 157.69, 160.12, 166.73, 172.79 ppm.

Infra-red spectroscopy, frequencies consist of at least wavelengths approximately 3359, 3281, 3197, 3067, 2926, approx. 1682 (shoulder), 1651, 1573, 1033, 1009 cm$^{-1}$. The term "approximately" means in this context that the cm$^{-1}$ values can vary, e.g. by up to ±1 cm$^{-1}$. The spectrum is presented in FIG. 10.

Ultra violet absorptions (10 μM) show absorption maxima at wavelengths 223 and 277 nm.

Accurate mass spectrometry; 454.1446 [M+H]$^+$ (1.97 ppm error) and 476.1266 [M+Na]$^+$ (0.29 ppm error).

LCMS: m/z=454.14, 456.10 (MH$^+$), RT=6.14 min. Consistent with natural abundance of chlorine isotopes $^{35}$Cl and $^{37}$Cl.

Physical Forms 2-4
In general, the tosylate salt (50 mg) was dissolved or slurried in a solvent/anti-solvent mix and shaken for 24 hours at −20° C. Details of the solvents are shown in the Table below. Resulting solids were isolated by removing the supernatant and drying the solids under vacuum. In experiments where precipitation was not observed, the solutions were concentrated by rotary evaporation to yield a precipitate which was filtered and dried under vacuum.

All samples were characterised by DSC (Method. 1, see data in Table below).

| Crystallisation Conditions | Assigned Form | DSC approximate onset temperature |
|---|---|---|
| Ethanol:Ethyl acetate (20:80) | Form 2 | 204° C. |
| Acetone:Acetonitrile (80:20) | Form 3 | 179° C. |
| Acetone:Octanol (60:40) | Form 3 | 179° C. |
| Acetone:Dioxane (40:60) | Form 4 | 170° C. |

All samples were analysed by XRPD (see FIGS. 2 to 4).
Peak Position Tables:
Tosylate Salt (Form 2)

| Pos. [°2Th.] | Height [cts] | FWHM [°2Th.] | d-spacing [Å] | Rel. Int. [%] | Tip width [°2Th.] |
|---|---|---|---|---|---|
| 5.5852 | 26.09 | 0.0590 | 15.81050 | 4.41 | 0.0708 |
| 6.7260 | 3.23 | 0.3149 | 13.13123 | 0.55 | 0.3779 |
| 7.8725 | 435.64 | 0.0984 | 11.22122 | 73.61 | 0.1181 |
| 8.2567 | 48.03 | 0.1181 | 10.69994 | 8.12 | 0.1417 |
| 9.1096 | 2.72 | 0.0787 | 9.69998 | 0.46 | 0.0945 |
| 10.8640 | 49.00 | 0.0590 | 8.13717 | 8.28 | 0.0708 |
| 11.0557 | 45.04 | 0.0590 | 7.99648 | 7.61 | 0.0708 |
| 11.2936 | 26.91 | 0.0394 | 7.82860 | 4.55 | 0.0472 |
| 11.6469 | 100.25 | 0.0984 | 7.59190 | 16.94 | 0.1181 |
| 11.8443 | 76.32 | 0.0984 | 7.46578 | 12.90 | 0.1181 |
| 12.3887 | 18.44 | 0.2362 | 7.13894 | 3.12 | 0.2834 |
| 13.6633 | 66.80 | 0.1574 | 6.47567 | 11.29 | 0.1889 |
| 15.1063 | 106.95 | 0.0590 | 5.86021 | 18.07 | 0.0708 |
| 15.2603 | 113.05 | 0.0787 | 5.80142 | 19.10 | 0.0945 |
| 16.4429 | 186.81 | 0.0787 | 5.38672 | 31.57 | 0.0945 |
| 16.5987 | 185.42 | 0.1181 | 5.33651 | 31.33 | 0.1417 |
| 17.6146 | 240.69 | 0.0984 | 5.03097 | 40.67 | 0.1181 |
| 17.8134 | 341.65 | 0.0787 | 4.97526 | 57.73 | 0.0945 |
| 18.0458 | 45.15 | 0.0787 | 4.91171 | 7.63 | 0.0945 |
| 18.5284 | 10.28 | 0.0787 | 4.78486 | 1.74 | 0.0945 |
| 19.3406 | 591.82 | 0.2362 | 4.58570 | 100.00 | 0.2834 |
| 20.2575 | 178.75 | 0.1440 | 4.38016 | 30.20 | 0.1728 |
| 21.2995 | 166.08 | 0.1200 | 4.16818 | 28.06 | 0.1440 |
| 21.6122 | 279.63 | 0.0960 | 4.10857 | 47.25 | 0.1152 |
| 22.6862 | 85.03 | 0.2400 | 3.91643 | 14.37 | 0.2880 |
| 23.2749 | 105.07 | 0.0960 | 3.81869 | 17.75 | 0.1152 |
| 23.6400 | 58.45 | 0.1920 | 3.76053 | 9.88 | 0.2304 |
| 24.3041 | 42.43 | 0.0960 | 3.65927 | 7.17 | 0.1152 |
| 24.5957 | 133.24 | 0.1200 | 3.61653 | 22.51 | 0.1440 |
| 25.0710 | 183.05 | 0.1680 | 3.54903 | 30.93 | 0.2016 |
| 25.5397 | 52.98 | 0.1440 | 3.48495 | 8.95 | 0.1728 |
| 26.0123 | 220.20 | 0.2160 | 3.42270 | 37.21 | 0.2592 |
| 26.2799 | 102.99 | 0.0720 | 3.38846 | 17.40 | 0.0864 |
| 26.7498 | 185.69 | 0.0960 | 3.32999 | 31.38 | 0.1152 |
| 27.1230 | 131.23 | 0.1200 | 3.28502 | 22.17 | 0.1440 |
| 27.9007 | 66.18 | 0.0720 | 3.19519 | 11.18 | 0.0864 |
| 28.5086 | 138.06 | 0.1200 | 3.12842 | 23.33 | 0.1440 |
| 28.9197 | 71.48 | 0.1440 | 3.08488 | 12.08 | 0.1728 |
| 29.9362 | 45.33 | 0.1200 | 2.98241 | 7.66 | 0.1440 |
| 30.4258 | 69.73 | 0.0720 | 2.93552 | 11.78 | 0.0864 |
| 30.8373 | 38.85 | 0.1920 | 2.89728 | 6.57 | 0.2304 |
| 31.2658 | 54.21 | 0.1920 | 2.85854 | 9.16 | 0.2304 |
| 31.5814 | 35.21 | 0.1440 | 2.83069 | 5.95 | 0.1728 |
| 32.1715 | 32.30 | 0.1200 | 2.78010 | 5.46 | 0.1440 |
| 32.8002 | 52.33 | 0.2400 | 2.72824 | 8.84 | 0.2880 |
| 33.1579 | 126.94 | 0.0960 | 2.69962 | 21.45 | 0.1152 |
| 34.0294 | 14.13 | 0.2880 | 2.63245 | 2.39 | 0.3456 |
| 34.6522 | 19.52 | 0.1440 | 2.58654 | 3.30 | 0.1728 |
| 35.8417 | 67.86 | 0.3840 | 2.50338 | 11.47 | 0.4608 |
| 36.5011 | 43.80 | 0.1920 | 2.45966 | 7.40 | 0.2304 |
| 37.6759 | 43.99 | 0.1440 | 2.38562 | 7.43 | 0.1728 |
| 38.2690 | 91.76 | 0.2400 | 2.35000 | 15.50 | 0.2880 |
| 39.8063 | 79.06 | 0.1440 | 2.26271 | 13.36 | 0.1728 |
| 40.7873 | 30.36 | 0.1920 | 2.21053 | 5.13 | 0.2304 |
| 41.5470 | 19.10 | 0.2400 | 2.17185 | 3.23 | 0.2880 |
| 42.7075 | 16.08 | 0.3840 | 2.11548 | 2.72 | 0.4608 |
| 43.9531 | 83.43 | 0.0720 | 2.05837 | 14.10 | 0.0864 |
| 44.9161 | 23.18 | 0.2880 | 2.01645 | 3.92 | 0.3456 |
| 45.5644 | 33.46 | 0.2400 | 1.98926 | 5.65 | 0.2880 |
| 45.9890 | 31.91 | 0.2400 | 1.97187 | 5.39 | 0.2880 |
| 46.6160 | 33.76 | 0.5760 | 1.94680 | 5.70 | 0.6912 |
| 46.8650 | 37.96 | 0.1440 | 1.93704 | 6.41 | 0.1728 |
| 47.6557 | 49.06 | 0.3840 | 1.90673 | 8.29 | 0.4608 |
| 48.1107 | 47.74 | 0.1920 | 1.88975 | 8.07 | 0.2304 |

Tosylate Salt (Form 3)

| Pos. [°2Th.] | Height [cts] | FWHM [°2Th.] | d-spacing [Å] | Rel. Int. [%] |
|---|---|---|---|---|
| 5.5427 | 19.32 | 0.1181 | 15.93150 | 4.50 |
| 7.6664 | 213.40 | 0.1378 | 11.52243 | 49.76 |
| 10.8685 | 43.47 | 0.0984 | 8.13378 | 10.14 |
| 11.3118 | 23.69 | 0.0590 | 7.81601 | 5.52 |
| 11.8783 | 71.63 | 0.1574 | 7.44451 | 16.70 |
| 12.4856 | 28.06 | 0.1181 | 7.08374 | 6.54 |
| 13.3728 | 17.56 | 0.1181 | 6.61569 | 4.10 |
| 14.9932 | 79.91 | 0.0787 | 5.90417 | 18.63 |
| 15.3422 | 103.94 | 0.0590 | 5.77062 | 24.24 |
| 15.7859 | 160.13 | 0.0984 | 5.60942 | 37.34 |
| 15.8954 | 112.39 | 0.0787 | 5.57101 | 26.20 |
| 16.6305 | 126.20 | 0.1181 | 5.32637 | 29.43 |
| 17.2303 | 105.21 | 0.0787 | 5.14229 | 24.53 |
| 17.5359 | 160.07 | 0.1181 | 5.05336 | 37.32 |
| 17.8852 | 87.61 | 0.1181 | 4.95546 | 20.43 |
| 18.5645 | 197.35 | 0.1378 | 4.77563 | 46.02 |
| 19.1490 | 94.84 | 0.0960 | 4.63116 | 22.11 |
| 19.2080 | 117.20 | 0.0590 | 4.61707 | 27.33 |
| 19.6616 | 14.04 | 0.1968 | 4.51156 | 3.27 |
| 20.3608 | 184.55 | 0.1574 | 4.35818 | 43.03 |
| 21.0420 | 221.33 | 0.0984 | 4.21860 | 51.61 |
| 21.7704 | 167.69 | 0.0984 | 4.07907 | 39.10 |
| 22.1229 | 75.35 | 0.0787 | 4.01487 | 17.57 |
| 22.4595 | 148.99 | 0.0787 | 3.95546 | 34.74 |
| 23.0876 | 156.55 | 0.0984 | 3.84924 | 36.50 |
| 23.7110 | 54.07 | 0.0787 | 3.74943 | 12.61 |
| 24.1983 | 37.32 | 0.2362 | 3.67502 | 8.70 |
| 24.9297 | 311.69 | 0.1200 | 3.56884 | 72.68 |
| 25.0295 | 428.88 | 0.1378 | 3.55483 | 100.00 |
| 26.0518 | 168.55 | 0.1378 | 3.41761 | 39.30 |
| 26.8205 | 77.14 | 0.3149 | 3.32138 | 17.99 |
| 27.5978 | 37.37 | 0.1968 | 3.22957 | 8.71 |
| 28.0013 | 46.02 | 0.1574 | 3.18393 | 10.73 |
| 28.4970 | 133.63 | 0.1968 | 3.12966 | 31.16 |
| 28.7856 | 43.70 | 0.0787 | 3.09894 | 10.19 |
| 29.6274 | 18.50 | 0.1574 | 3.01278 | 4.31 |
| 30.9028 | 28.47 | 0.1968 | 2.89129 | 6.64 |
| 31.8038 | 42.81 | 0.1968 | 2.81140 | 9.98 |
| 32.9329 | 47.70 | 0.1574 | 2.71755 | 11.12 |
| 33.9440 | 12.89 | 0.1968 | 2.63888 | 3.00 |
| 34.7539 | 37.92 | 0.1968 | 2.57921 | 8.84 |
| 36.1237 | 20.57 | 0.0984 | 2.48449 | 4.80 |
| 36.9574 | 18.49 | 0.2362 | 2.43034 | 4.31 |
| 37.6271 | 25.80 | 0.1574 | 2.38860 | 6.02 |
| 38.1091 | 30.58 | 0.1968 | 2.35949 | 7.13 |

| Pos. [°2Th.] | Height [cts] | FWHM [°2Th.] | d-spacing [Å] | Rel. Int. [%] |
|---|---|---|---|---|
| 38.6076 | 10.76 | 0.1968 | 2.33016 | 2.51 |
| 39.8057 | 16.11 | 0.9446 | 2.26275 | 3.76 |
| 40.8286 | 12.41 | 0.0984 | 2.20839 | 2.89 |
| 41.1459 | 7.04 | 0.6298 | 2.19209 | 1.64 |
| 42.5236 | 30.34 | 0.1968 | 2.12420 | 7.07 |
| 43.9909 | 27.09 | 0.2362 | 2.05669 | 6.32 |
| 45.1491 | 10.17 | 0.1574 | 2.00659 | 2.37 |
| 45.7194 | 28.71 | 0.2362 | 1.98288 | 6.69 |
| 46.3312 | 21.00 | 0.1968 | 1.95810 | 4.90 |
| 48.2114 | 14.83 | 0.1920 | 1.88604 | 3.46 |

Tosylate Salt (Form 4)

| Pos. [°2Th.] | Height [cts] | FWHM [°2Th.] | d-spacing [Å] | Rel. Int. [%] |
|---|---|---|---|---|
| 7.7464 | 174.31 | 0.1181 | 11.40356 | 49.85 |
| 10.7629 | 100.88 | 0.1181 | 8.21333 | 28.85 |
| 11.1226 | 38.60 | 0.0590 | 7.94855 | 11.04 |
| 11.7735 | 51.39 | 0.1181 | 7.51053 | 14.70 |
| 12.4248 | 7.69 | 0.1574 | 7.11828 | 2.20 |
| 13.1511 | 17.41 | 0.1181 | 6.72672 | 4.98 |
| 14.6024 | 45.10 | 0.1968 | 6.06127 | 12.90 |
| 15.4450 | 129.55 | 0.0787 | 5.73245 | 37.05 |
| 15.6113 | 135.32 | 0.0590 | 5.67174 | 38.70 |
| 15.9392 | 96.72 | 0.1181 | 5.55582 | 27.66 |
| 16.7372 | 72.73 | 0.0787 | 5.29267 | 20.80 |
| 16.8295 | 79.44 | 0.0590 | 5.26386 | 22.72 |
| 17.1153 | 68.92 | 0.1574 | 5.17657 | 19.71 |
| 17.7858 | 226.01 | 0.1378 | 4.98293 | 64.64 |
| 18.0639 | 62.60 | 0.1181 | 4.90681 | 17.90 |
| 18.8021 | 241.42 | 0.1181 | 4.71580 | 69.05 |
| 19.2754 | 174.67 | 0.1378 | 4.60107 | 49.95 |
| 19.9134 | 24.52 | 0.1181 | 4.45507 | 7.01 |
| 20.5634 | 210.44 | 0.1574 | 4.31569 | 60.19 |
| 20.8227 | 187.80 | 0.1378 | 4.26252 | 53.71 |
| 21.2636 | 201.68 | 0.1181 | 4.17514 | 57.68 |
| 21.6334 | 213.61 | 0.1968 | 4.10459 | 61.09 |
| 22.2111 | 117.30 | 0.0984 | 3.99912 | 33.55 |
| 22.6910 | 32.27 | 0.0394 | 3.91562 | 9.23 |
| 23.4259 | 182.97 | 0.0984 | 3.79442 | 52.33 |
| 23.8408 | 76.08 | 0.1574 | 3.72932 | 21.76 |
| 24.2765 | 173.88 | 0.1378 | 3.66337 | 49.73 |
| 24.8450 | 349.65 | 0.1181 | 3.58081 | 100.00 |
| 25.5485 | 38.62 | 0.1574 | 3.48378 | 11.05 |
| 25.6937 | 53.02 | 0.0590 | 3.46441 | 15.16 |
| 26.3244 | 171.38 | 0.0590 | 3.38283 | 49.01 |
| 26.8167 | 71.60 | 0.1968 | 3.32183 | 20.48 |
| 27.2923 | 64.28 | 0.1574 | 3.26502 | 18.39 |
| 27.5244 | 26.77 | 0.0984 | 3.23802 | 7.66 |
| 27.8961 | 70.69 | 0.2362 | 3.19570 | 20.22 |
| 28.3790 | 180.78 | 0.1771 | 3.14241 | 51.70 |
| 29.0096 | 44.09 | 0.0787 | 3.07553 | 12.61 |
| 29.8649 | 48.54 | 0.1574 | 2.98936 | 13.88 |
| 30.2431 | 39.86 | 0.0590 | 2.95284 | 11.40 |
| 30.7704 | 19.29 | 0.0787 | 2.90342 | 5.52 |
| 31.1063 | 20.06 | 0.1181 | 2.87283 | 5.74 |
| 31.5035 | 17.78 | 0.1574 | 2.83751 | 5.08 |
| 31.8259 | 41.68 | 0.0590 | 2.80950 | 11.92 |
| 32.1507 | 45.97 | 0.1968 | 2.78185 | 13.15 |
| 32.5549 | 18.36 | 0.1181 | 2.74824 | 5.25 |
| 33.2454 | 25.53 | 0.1574 | 2.69271 | 7.30 |
| 33.9996 | 29.07 | 0.1968 | 2.63468 | 8.31 |
| 34.3994 | 30.21 | 0.1574 | 2.60497 | 8.64 |
| 34.7436 | 17.87 | 0.1968 | 2.57995 | 5.11 |
| 35.4357 | 32.82 | 0.2755 | 2.53113 | 9.39 |
| 36.4511 | 13.59 | 0.2362 | 2.46292 | 3.89 |
| 37.0563 | 36.56 | 0.1968 | 2.42408 | 10.46 |
| 38.1537 | 37.61 | 0.1968 | 2.35684 | 10.76 |
| 38.5425 | 24.30 | 0.1968 | 2.33395 | 6.95 |
| 39.1407 | 9.10 | 0.1968 | 2.29965 | 2.60 |
| 40.3633 | 20.73 | 0.3149 | 2.23277 | 5.93 |
| 40.8758 | 17.67 | 0.1968 | 2.20595 | 5.05 |
| 41.7350 | 9.28 | 0.3936 | 2.16250 | 2.65 |
| 43.2701 | 41.85 | 0.0787 | 2.08927 | 11.97 |
| 44.0503 | 19.05 | 0.1574 | 2.05406 | 5.45 |
| 44.6658 | 27.99 | 0.0984 | 2.02717 | 8.01 |
| 46.4165 | 24.71 | 0.1968 | 1.95471 | 7.07 |
| 47.7596 | 28.50 | 0.0590 | 1.90282 | 8.15 |
| 48.6633 | 16.95 | 0.1920 | 1.86958 | 4.85 |

NMR data showed that all samples were present as the salt and that the stoichiometry was 1:1. Microanalysis data (C, H, N) also confirmed formation of salt (see Table below).

| Sample Name | Theoretical Carbon % | Theoretical Hydrogen % | Theoretical Nitrogen % | Experimental Carbon % | Experimental Hydrogen % | Experimental Nitrogen % |
|---|---|---|---|---|---|---|
| Form 2 | 57.55 | 4.67 | 11.19 | 57.65 | 4.57 | 10.89 |
|  |  |  |  | 57.55 | 4.40 | 11.01 |
| Form 3 | 57.55 | 4.67 | 11.19 | 57.53 | 4.68 | 10.89 |
|  |  |  |  | 57.58 | 4.59 | 10.79 |
| Form 4 | 57.55 | 4.67 | 11.19 | 57.88 | 4.42 | 10.90 |
|  |  |  |  | 57.91 | 4.45 | 10.80 |

Physical Form 5

A solution of the tosylate salt was prepared (100 mg/ml) in methanol. An aliquot was were dispensed into a 96-well plate and 1 ml of tetrahydrofuran (THF) was added to afford a precipitate. The excess solvent was decanted and the crystals dried under vacuum for 24 hours.

The sample was analysed by XRPD (see FIG. 5).

| Peak position table: | | | | |
|---|---|---|---|---|
| Pos. [°2Th.] | Height [cts] | FWHM [°2Th.] | d-spacing [Å] | Rel. Int. [%] |
| 7.3122 | 14.69 | 0.1440 | 12.07977 | 1.28 |
| 7.7267 | 199.08 | 0.0960 | 11.43258 | 17.38 |
| 10.6654 | 37.31 | 0.1200 | 8.28825 | 3.26 |
| 10.9989 | 16.81 | 0.0960 | 8.03768 | 1.47 |
| 11.6970 | 56.50 | 0.1200 | 7.55951 | 4.93 |
| 13.1713 | 13.19 | 0.1440 | 6.71648 | 1.15 |
| 14.8084 | 33.32 | 0.0960 | 5.97740 | 2.91 |
| 15.2775 | 21.64 | 0.1440 | 5.79490 | 1.89 |
| 15.8331 | 75.68 | 0.1920 | 5.59279 | 6.61 |
| 16.4901 | 42.86 | 0.1200 | 5.37140 | 3.74 |
| 17.0849 | 44.58 | 0.1440 | 5.18574 | 3.89 |
| 17.5974 | 112.11 | 0.0720 | 5.03585 | 9.79 |
| 17.7682 | 326.91 | 0.0960 | 4.98782 | 28.53 |
| 17.9881 | 57.47 | 0.0720 | 4.92732 | 5.02 |
| 18.7855 | 245.04 | 0.0720 | 4.71994 | 21.39 |
| 19.1215 | 176.17 | 0.0720 | 4.63776 | 15.38 |
| 20.1045 | 32.55 | 0.0720 | 4.41316 | 2.84 |
| 20.3338 | 238.61 | 0.1440 | 4.36390 | 20.83 |
| 21.0330 | 450.80 | 0.0960 | 4.22039 | 39.35 |
| 21.3713 | 130.40 | 0.0960 | 4.15434 | 11.38 |
| 21.8860 | 102.96 | 0.0960 | 4.05778 | 8.99 |
| 22.2900 | 53.55 | 0.3840 | 3.98514 | 4.67 |
| 22.5102 | 88.18 | 0.0720 | 3.94666 | 7.70 |
| 23.1729 | 821.45 | 0.0960 | 3.83526 | 71.70 |
| 23.7535 | 19.03 | 0.1440 | 3.74283 | 1.66 |
| 24.4843 | 602.56 | 0.0960 | 3.63273 | 52.59 |
| 25.0518 | 893.76 | 0.0720 | 3.55172 | 78.01 |
| 25.3986 | 48.62 | 0.1440 | 3.50400 | 4.24 |
| 26.0294 | 322.02 | 0.0720 | 3.42049 | 28.11 |
| 26.1248 | 204.21 | 0.0720 | 3.40822 | 17.82 |
| 26.3520 | 34.60 | 0.1440 | 3.37934 | 3.02 |
| 26.8291 | 157.69 | 0.0960 | 3.32033 | 13.76 |
| 27.0090 | 43.52 | 0.1440 | 3.29861 | 3.80 |
| 27.2457 | 48.33 | 0.0720 | 3.27050 | 4.22 |
| 27.6954 | 38.75 | 0.2880 | 3.21840 | 3.38 |
| 28.1703 | 619.57 | 0.0960 | 3.16522 | 54.08 |
| 28.4843 | 1145.67 | 0.0720 | 3.13104 | 100.00 |
| 28.7755 | 39.00 | 0.1200 | 3.10001 | 3.40 |
| 29.0781 | 14.63 | 0.0960 | 3.06844 | 1.28 |
| 29.9202 | 28.82 | 0.1440 | 2.98396 | 2.52 |
| 30.2441 | 67.61 | 0.0720 | 2.95274 | 5.90 |
| 31.7100 | 19.95 | 0.1920 | 2.81950 | 1.74 |
| 32.1902 | 32.32 | 0.2400 | 2.77853 | 2.82 |
| 33.1033 | 65.99 | 0.1440 | 2.70394 | 5.76 |
| 33.4701 | 10.82 | 0.1200 | 2.67515 | 0.94 |
| 33.8603 | 15.44 | 0.0720 | 2.64521 | 1.35 |
| 34.5200 | 29.37 | 0.0720 | 2.59615 | 2.56 |
| 34.9430 | 6.91 | 0.0720 | 2.56569 | 0.60 |
| 35.2950 | 51.56 | 0.0720 | 2.54090 | 4.50 |
| 35.7611 | 68.67 | 0.1680 | 2.50884 | 5.99 |
| 35.9963 | 18.91 | 0.0720 | 2.49299 | 1.65 |
| 36.5789 | 47.00 | 0.0960 | 2.45460 | 4.10 |
| 36.9113 | 45.66 | 0.1200 | 2.43326 | 3.99 |
| 37.3909 | 40.57 | 0.0960 | 2.40315 | 3.54 |
| 37.6249 | 200.47 | 0.0720 | 2.38874 | 17.50 |
| 38.0512 | 17.03 | 0.0720 | 2.36295 | 1.49 |
| 38.6741 | 12.69 | 0.1440 | 2.32631 | 1.11 |
| 39.1034 | 16.38 | 0.1920 | 2.30175 | 1.43 |
| 39.8265 | 20.21 | 0.1200 | 2.26162 | 1.76 |
| 40.5267 | 13.55 | 0.0720 | 2.22414 | 1.18 |
| 41.2363 | 16.75 | 0.1200 | 2.18749 | 1.46 |
| 42.4350 | 6.36 | 0.0960 | 2.12843 | 0.55 |
| 42.8444 | 30.67 | 0.1200 | 2.10904 | 2.68 |
| 43.6166 | 10.45 | 0.1440 | 2.07347 | 0.91 |
| 44.1443 | 7.70 | 0.1680 | 2.04990 | 0.67 |
| 44.3130 | 9.78 | 0.0720 | 2.04249 | 0.85 |
| 44.5519 | 13.83 | 0.0960 | 2.03209 | 1.21 |
| 44.7737 | 3.56 | 0.0960 | 2.02253 | 0.31 |
| 45.0260 | 27.09 | 0.0720 | 2.01179 | 2.36 |
| 45.2231 | 49.65 | 0.0720 | 2.00348 | 4.33 |
| 45.3734 | 7.16 | 0.0960 | 1.99719 | 0.62 |
| 45.8825 | 20.30 | 0.1440 | 1.97620 | 1.77 |
| 46.4636 | 23.62 | 0.1440 | 1.95283 | 2.06 |
| 47.3681 | 45.09 | 0.0720 | 1.91763 | 3.94 |
| 47.9143 | 10.89 | 0.1440 | 1.89704 | 0.95 |
| 48.2134 | 22.67 | 0.1440 | 1.88597 | 1.98 |
| 48.6051 | 5.32 | 0.0960 | 1.87168 | 0.46 |

Melting point approximately 183° C./204° C. (DSC Method 1, onset temperature). It is suspected that initially the sample is a THF solvate which desolvates on heating to yield a mixture of two polymorphic forms.

Microanalysis (1); C 57.56%, H 4.63%, N 10.81%
Microanalysis (2); C 57.48%, H 4.82%, N 10.78%
(Theoretical; C 57.55%, H 4.67%, 11.19%)

Physical Form 6

Cyclopropanecarboxylic acid 4-(6-chloro-3-methyl-4,10-dihydro-3H-2,3,4,9-tetraazabenzo[f]azulene-9-carbonyl)-2-fluoro-benzylamide (72.50 g) was placed in a reactor vessel. To this was added 300 mL of an 8.1% aqueous methyl ethyl ketone (MEK) solution and the mixture stirred and warmed to 25° C. Stirring was maintained at 25° C. for approximately 15 minutes. To this was added a solution of para-toluenesulfonic acid monohydrate (30.38 g) in MEK (200 mL) in one portion. The mixture was stirred at 20-25° C. for 5 hours at which point it was a homogeneous solution. The solution was left overnight at 20-25° C. to give a precipitate. 250 mL of 6% aqueous MEK was added. The mixture cleared somewhat and after stirring for 30 minutes another 250 mL of 6% MEK was added at which point the mixture became a coloured solution. The solution was cooled to 40° C. Meanwhile a seeding suspension of the title compound (1 g; Form 1, prepared using the method described herein above) in 10 mL MEK (conc 100 mg ml$^{-1}$) was prepared.

Once the vessel had been stable at 40° C. for 30 minutes the seeding suspension was added. The seeds were observed to persist and then 2000 mL of MEK was added over a period of 3 minutes and 5 seconds. The temperature of the mixture dropped to 30.0° C. The jacket was maintained at 40° C. for 5 minutes (the vessel warmed back up to 41.8° C. before cooling) and then the jacket was set to 10° C. The mixture was stirred for 90 minutes at 10° C. Stirring was stopped and the solid material settled rapidly on the bottom. The solid was drained from the vessel and filtered. The vessel and solid were washed with 250 mL of MEK and the solid was air dried. NMR analysis indicated the presence of approximately 0.76 mole equivalents of MEK.

The sample was analysed by XRPD (see FIG. 6).

| Peak position table: | | | | |
|---|---|---|---|---|
| Pos. [°2Th.] | Height [cts] | FWHM [°2Th.] | d-spacing [Å] | Rel. Int. [%] |
| 7.5268 | 254.83 | 0.1506 | 11.74556 | 16.82 |
| 10.6994 | 168.12 | 0.1673 | 8.26885 | 12.33 |
| 11.0944 | 69.45 | 0.09 | 7.97532 | 1.85 |
| 11.6702 | 139.88 | 0.184 | 7.58304 | 11.28 |

-continued

Peak position table:

| Pos. [°2Th.] | Height [cts] | FWHM [°2Th.] | d-spacing [Å] | Rel. Int. [%] |
|---|---|---|---|---|
| 12.3022 | 67.46 | 0.2007 | 7.1949 | 5.94 |
| 13.0324 | 42.97 | 0.09 | 6.79337 | 1.15 |
| 14.7597 | 212.14 | 0.1151 | 6.002 | 7.23 |
| 15.122 | 317.65 | 0.2456 | 5.859 | 23.12 |
| 15.5145 | 432.35 | 0.2342 | 5.71166 | 44.39 |
| 16.4628 | 289.31 | 0.1506 | 5.3847 | 19.1 |
| 16.8287 | 305.55 | 0.1673 | 5.26844 | 22.41 |
| 17.3235 | 395.22 | 0.184 | 5.11907 | 31.88 |
| 17.7286 | 293.75 | 0.184 | 5.00301 | 23.7 |
| 18.1946 | 577.32 | 0.184 | 4.87591 | 46.57 |
| 18.8746 | 390.14 | 0.184 | 4.70175 | 31.47 |
| 19.4744 | 192.15 | 0.008 | 4.55828 | 0.46 |
| 20.1057 | 584.8 | 0.2007 | 4.41656 | 51.47 |
| 20.7827 | 675 | 0.184 | 4.27417 | 54.45 |
| 21.5675 | 556.89 | 0.184 | 4.12039 | 44.93 |
| 22.0003 | 499.06 | 0.2165 | 4.0403 | 32.02 |
| 22.2831 | 460.5 | 0.1506 | 3.98967 | 30.29 |
| 22.9434 | 477.47 | 0.1673 | 3.87632 | 35.02 |
| 23.9267 | 183.43 | 0.2007 | 3.71919 | 16.14 |
| 24.8662 | 1239.6 | 0.184 | 3.58077 | 100 |
| 25.879 | 599.78 | 0.184 | 3.44288 | 48.39 |
| 26.6163 | 293.07 | 0.2676 | 3.34916 | 34.39 |
| 27.2838 | 321.58 | 0.2799 | 3.26872 | 26.66 |
| 28.3587 | 323.65 | 0.1673 | 3.14723 | 23.74 |
| 29.4387 | 130.49 | 0.2007 | 3.03418 | 11.48 |
| 32.0689 | 101.83 | 0.2676 | 2.79107 | 11.95 |
| 32.7612 | 87.36 | 0.2676 | 2.73366 | 10.25 |

Infra-red spectroscopy, frequencies consist of at least wavelengths approximately 1653, 1549, 1497, 1443, 1420, 1382, 1320, 1223, 1149, 1123, 1032, 1008, 931, 811, 683 cm$^{-1}$. The spectrum is presented in FIG. 11.

Melting point 201° C. (DSC Method 2, onset temperature)

Physical Form 7

The tosylate salt (6 g, 9.6 mmol) was taken up in a mixture of water (0.9 mL) and methyl ethyl ketone (MEK) (14.1 mL) and warmed to 74° C. at a rate of 2° C. per minute. The mixture was maintained at 74° C. for 45 minutes then aliquots of water (0.05 mL per aliquot) were added while stirring until the solid had dissolved. The mixture was cooled to 5° C. at a rate of 0.1° C. per minute and maintained at 5° C. for 5 hours. The mixture was warmed to 20° C. at a rate of 0.1° C. The final composition was a concentration of tosylate salt of 391 mg/mL in a mixture of 8.1% water in MEK. The solid was filtered to afford an off-white solid (yield 3 g, 50%).

The sample was analysed by XRPD (see FIG. 7).

Peak position table:

| Pos. [°2Th.] | Height [cts] | FWHM [°2Th.] | d-spacing [Å] | Rel. Int. [%] |
|---|---|---|---|---|
| 6.1474 | 105 | 0.09 | 14.37777 | 0.99 |
| 6.8148 | 644.02 | 0.1338 | 12.97102 | 13.33 |
| 7.8503 | 1206.13 | 0.1506 | 11.26229 | 28.08 |
| 8.1252 | 341.77 | 0.1338 | 10.88188 | 7.07 |
| 10.6014 | 111.29 | 0.09 | 8.34507 | 1.05 |
| 11.3073 | 158.97 | 0.3346 | 7.82563 | 8.22 |
| 12.1516 | 169.97 | 0.3346 | 7.28372 | 8.79 |
| 12.9644 | 483.78 | 0.1673 | 6.82882 | 12.51 |
| 13.6842 | 662.54 | 0.1673 | 6.47122 | 17.14 |
| 14.2976 | 152.64 | 0.2007 | 6.19491 | 4.74 |
| 15.0887 | 217.03 | 0.2007 | 5.87185 | 6.74 |
| 15.8193 | 660.93 | 0.2175 | 5.60229 | 22.22 |
| 16.3717 | 501.82 | 0.2007 | 5.41448 | 15.58 |
| 17.0471 | 366.31 | 0.2175 | 5.20144 | 12.32 |
| 17.8315 | 680.12 | 0.2175 | 4.97437 | 22.87 |
| 18.4672 | 938.82 | 0.1673 | 4.80454 | 24.28 |
| 19.3201 | 864.99 | 0.2342 | 4.59431 | 31.32 |
| 19.8882 | 1672.82 | 0.1338 | 4.46436 | 34.61 |
| 20.1449 | 2663.32 | 0.184 | 4.40805 | 75.78 |
| 20.7025 | 1267.07 | 0.3346 | 4.29055 | 65.55 |
| 21.2592 | 987.57 | 0.2007 | 4.17944 | 30.65 |
| 21.6178 | 1365.29 | 0.1673 | 4.11092 | 35.31 |
| 22.192 | 417.94 | 0.1673 | 4.00584 | 10.81 |
| 23.1692 | 1907.55 | 0.184 | 3.83905 | 54.27 |
| 23.5444 | 1390.9 | 0.1506 | 3.77871 | 32.38 |
| 23.8075 | 808.19 | 0.1673 | 3.73755 | 20.9 |
| 24.2515 | 434.92 | 0.1338 | 3.67012 | 9 |
| 24.7094 | 418.2 | 0.3346 | 3.60314 | 21.63 |
| 25.5013 | 761.14 | 0.184 | 3.49301 | 21.66 |
| 26.4566 | 3221.84 | 0.2007 | 3.36902 | 100 |
| 26.947 | 1325.81 | 0.184 | 3.30881 | 37.72 |
| 27.3602 | 726.18 | 0.2007 | 3.25977 | 22.54 |
| 29.1332 | 446.38 | 0.1506 | 3.06529 | 10.39 |
| 29.4254 | 415.87 | 0.1338 | 3.03552 | 8.61 |
| 29.9127 | 285.04 | 0.2676 | 2.98716 | 11.8 |
| 30.7424 | 703.89 | 0.2007 | 2.90841 | 21.85 |
| 31.148 | 607.52 | 0.1673 | 2.87146 | 15.71 |
| 32.1517 | 546.14 | 0.184 | 2.78408 | 15.54 |
| 32.6953 | 720.09 | 0.184 | 2.73902 | 20.49 |
| 33.0889 | 494.23 | 0.1673 | 2.70733 | 12.78 |
| 34.8881 | 93.45 | 0.5353 | 2.57172 | 7.73 |
| 36.2086 | 236.89 | 0.2007 | 2.48091 | 7.35 |
| 36.6135 | 384.94 | 0.1673 | 2.4544 | 9.96 |
| 39.6676 | 184.74 | 0.2007 | 2.27219 | 5.73 |
| 40.2478 | 305.04 | 0.2007 | 2.24076 | 9.47 |
| 42.1142 | 102.96 | 0.4015 | 2.14567 | 6.39 |
| 44.381 | 159.89 | 0.3011 | 2.0412 | 7.44 |
| 46.8935 | 66.01 | 0.4896 | 1.93593 | 6.75 |

Infra-red spectroscopy, frequencies consist of at least wavelengths approximately 1675, 1656, 1625, 1572, 1500, 1418, 1378, 1298, 1221, 1154, 1123, 1092, 1035, 1011, 935, 890, 866, 813, 683 cm$^{-1}$. The spectrum is presented in FIG. 12.

Melting point 200° C. (DSC Method 2, onset temperature)

Solubility

A comparison of the thermodynamic solubilities of cyclopropanecarboxylic acid 4-(6-chloro-3-methyl-4,10-dihydro-3H-2,3,4,9-tetraazabenzo[f]azulene-9-carbonyl)-2-fluoro-benzylamide (free base) and cyclopropanecarboxylic acid 4-(6-chloro-3-methyl-4,10-dihydro-3H-2,3,4,9-tetraaza-benzo[f]azulene-9-carbonyl)-2-fluoro-benzylamide para-toluenesulphonate (tosylate) was carried out. A spectrophotometric method was used. Standards were prepared in methanol (including a methanol blank) and the absorbance measured at 260 and 270 nm, from which a calibration line was generated for each wavelength. The test compound was incubated with agitation in water at 37° C. for 24 h before removal of non-soluble material by centrifugation. The supernatant was analysed against the calibration lines (after subtraction of the water blank response) and the mean of the determinations at the two wavelengths was reported.

The results were as follows:

| Form | Solubility (µg/ml) in water |
|---|---|
| Free base | 5 |
| Tosylate | 40 |

Oral Availability

Figure 9:
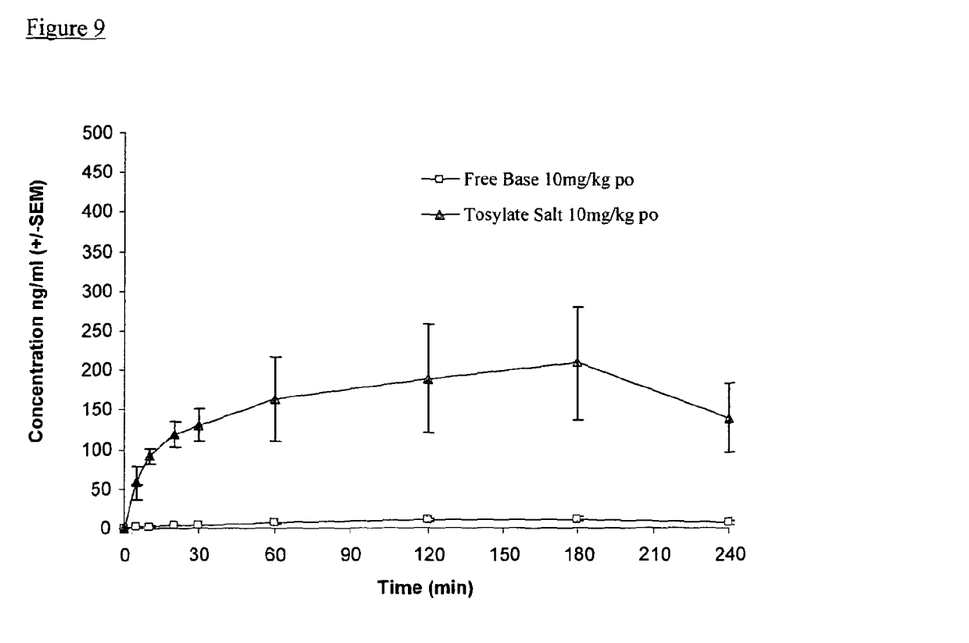
FIG. 9: Plasma exposures following oral administration of cyclopropanecarboxylic acid 4-(6-chloro-3-methyl-4,10-dihydro-3H-2,3,4,9-tetraazabenzo[f]azulene-9-carbonyl)-2-fluoro-benzylamide (free base) and cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate (tosylate salt) in 0.5% HPMC (n=4/group)

The plasma exposure in rats following dosing with the cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate ("Tosylate") has been examined in comparison with the corresponding free base, cyclopropanecarboxylic acid 4-(6-chloro-3-methyl-4,10-dihydro-3H-2,3,4,9-tetraazabenzo[f]azulene-9-carbonyl)-2-fluoro-benzylamide ("Free Base"). Suspensions of the Tosylate and Free Base were administered in 0.5% HPMC at 10 mg/kg p.o. Results are shown in FIG. 9. As a suspension, the Free Base is minimally absorbed however the Tosylate reaches a $C_{max}$ of 209 ng/mL and $AUC_{last}$ equals 40204 min·ng/mL.

Biological Activity

The ability of the tosylate salt of the invention to inhibit the vasopressin $V_{1a}$ receptor may be determined using the in vitro functional calcium mobilisation assay (FLIPR) described in PCT/DK2005/000540. This assay measures antagonist activity at a cloned human $V_{1a}$ receptor.

When tested in this assay the tosylate salt of the present invention showed a mean fpKi (Human V1a) of 8.5.

The invention claimed is:

1. A solid form of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate which exhibits at least the following characteristic X-ray powder diffraction peaks (Cu Kα radiation, expressed in degrees 2θ) at approximately 8.2, 12.2, 17.2, 21.4, 23.3 and 25.8.

2. The solid form according to claim 1, having an X-ray powder diffraction pattern substantially the same as that shown in FIG. 1.

3. The solid form of claim 1, which is characterised by an IR spectrum having characteristic peaks expressed in cm$^{-1}$ at approximately 3359, 3281, 3197, 3067, 2926, approx. 1682 (shoulder), 1651, 1573, 1033 and 1009.

4. The solid form according to claim 3 having an infrared spectrum substantially the same as that shown in FIG. 10.

5. A solid form of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, which exhibits at least the following characteristic X-ray powder diffraction peaks (Cu Kα radiation, expressed in degrees 2θ) at approximately 7.9, 16.4, 17.8, 19.3, 21.6 and 25.1.

6. The solid form according to claim 5 having an X-ray powder diffraction pattern substantially the same as that shown in FIG. 2.

7. A solid form of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, which exhibits at least the following characteristic X-ray powder diffraction peaks (Cu Kα radiation, expressed in degrees 2θ) at approximately 7.7, 15.8, 18.6, 20.4, 24.9 and 25.0.

8. The solid form according to claim 7 having an X-ray powder diffraction pattern substantially the same as that shown in FIG. 3.

9. A solid form of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, which exhibits at least the following characteristic X-ray powder diffraction peaks (Cu Kα radiation, expressed in degrees 2θ) at approximately 10.8, 15.5, 18.8, 21.3, 21.6 and 24.9.

10. The solid form according to claim 9 having an X-ray powder diffraction pattern substantially the same as that shown in FIG. 4.

11. A solid form of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, which exhibits at least the following characteristic X-ray powder diffraction peaks (Cu Kα radiation, expressed in degrees 2θ) at approximately 7.7, 17.8, 20.3, 23.2, 28.2 and 28.5.

12. The solid form according to claim 11 having an X-ray powder diffraction pattern substantially the same as that shown in FIG. 5.

13. A solid form of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, which exhibits at least the following characteristic X-ray powder diffraction peaks (Cu Kα radiation, expressed in degrees 2θ) at approximately 15.5, 18.2, 20.1, 20.8, 21.6 and 25.9.

14. The solid form according to claim 13 having an X-ray powder diffraction pattern substantially the same as that shown in FIG. 6.

15. The solid form of claim 13, which is characterised by an infrared spectrum having characteristic peaks expressed in cm$^{-1}$ at approximately 1653, 1549, 1497, 1443, 1420, 1382, 1320, 1223, 1149, 1123, 1032, 1008, 931, 811 and 683.

16. The solid form according to claim 15 having an IR spectrum substantially the same as that shown in FIG. 11.

17. A solid form of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate, which exhibits at least the following characteristic X-ray powder diffraction peaks (Cu Kα radiation, expressed in degrees 2θ) at approximately 7.9, 15.8, 20.1, 21.6, 23.5 and 32.7.

18. The solid form according to claim 17 having an X-ray powder diffraction pattern substantially the same as that shown in FIG. 7.

19. The solid form of claim 17, which is characterised by an infrared spectrum having characteristic peaks expressed in cm$^{-1}$ at approximately 1675, 1656, 1625, 1572, 1500, 1418, 1378, 1298, 1221, 1154, 1123, 1092, 1035, 1011, 935, 890, 866, 813 and 683.

20. The solid form according to claim 19 having an IR spectrum substantially the same as that shown in FIG. 12.

21. A pharmaceutical composition comprising cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate and a pharmaceutically acceptable adjuvant, diluent or carrier, in which the cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate in the composition is the solid form of any one of claims 1, 3, 5, 7, 9, 11, 13, 15, 17, or 19.

22. A method of treatment of a disease or condition mediated by vasopressin $V_{1a}$ receptors, said method comprising administering to a mammal in need of such treatment a therapeutically effective amount of the solid form of cyclopropanecarboxylic acid 4-(6-chloro-3-methyl-4,10-dihydro-3H-2,3,4,9-tetraazabenzo[f]azulene-9-carbonyl)-2-fluoro-benzylamide para-toluenesulphonate according to any one of claims 1, 3, 5, 7, 9, 11, 13, 15, 17, or 19, wherein said disease or condition mediated by vasopressin $V_{1a}$ receptors is dysmenorrhoea.

* * * * *